United States Patent
Gingera et al.

(10) Patent No.: US 8,754,290 B2
(45) Date of Patent: Jun. 17, 2014

(54) HO/LL CANOLA WITH RESISTANCE TO CLUBROOT DISEASE

(75) Inventors: Gregory R. Gingera, Saskatchewan (CA); Jianwei Zhao, Saskatchewan (CA); Van Leonard Ripley, Saskatchewan (CA); Lasantha Ubayasena, Lafayette, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 97 days.

(21) Appl. No.: 13/246,757

(22) Filed: Sep. 27, 2011

(65) Prior Publication Data

US 2012/0204286 A1     Aug. 9, 2012

Related U.S. Application Data

(63) Continuation-in-part of application No. 13/024,232, filed on Feb. 9, 2011, now abandoned.

(51) Int. Cl.
*A01H 1/04* (2006.01)
*C12Q 1/68* (2006.01)

(52) U.S. Cl.
USPC ................ 800/267; 800/265; 435/6.11

(58) Field of Classification Search
None
See application file for complete search history.

(56) References Cited

U.S. PATENT DOCUMENTS

2009/0202703 A1    8/2009    Despeghel et al.

FOREIGN PATENT DOCUMENTS

WO    2011060946 A1    5/2011

OTHER PUBLICATIONS

Nevin Dale Young. 1999. A cautiously optimistic vision for marker-assisted breeding. Molecular Breeding. 5:505-510.*
Hasan et al. 2008. Association of gene-linked SSR markers to seed glucosinolate content in oilseed rap (*Brassica napus* ssp. napus). Theor Appl Genet. 116:1035-1049.*
Piao et al. 2009. Genetics of clubroot resistance in *Brassica* species. J. Plant Growth Regul. 28:252-264.*
GenBank. 2002. Accession AF056570. p. 1-2.*
International Search Report and Written Opinion for PCT application No. PCT/US2012/057574, mailed Mar. 13, 2013.
Nesi et al., Genetic and molecular approaches to improve nutritional value of *Brassica napus* L. seed, C.R. Biologies, Sep. 4, 2008, vol. 331, No. 10, pp. 763-771.

* cited by examiner

*Primary Examiner* — Cathy Kingdon Worley
*Assistant Examiner* — Jeffrey Bolland
(74) *Attorney, Agent, or Firm* — Marcia J. Rosenfeld; TraskBritt, P.C.

(57) ABSTRACT

This disclosure concerns a plant of the genus, *Brassica*, or parts thereof, which comprise one or more traits selected from the group consisting of high oleic acid content, low linolenic acid content, increased herbicide resistance, restorer of cytoplasmic male sterility, and increased clubroot disease (*Plasmodiophora brassicae*) resistance, compared to a wild-type plant of the same species. This disclosure further relates to wild-type and mutant alleles of genes involved in these traits, molecular markers linked thereto, and methods of their use.

3 Claims, 10 Drawing Sheets

```
  1 CAATCCCTCGCTCTTTCTCCTACCTCATCTGGGACATCATCATAGCCTCC  50
    ||||||||||||||||||||||||||||||||||||||||||||||||||
  1 CAATCCCTCGCTCTTTCTCCTACCTCATCTGGGACATCATCATAGCCTCC  50

51 TGCTTCTACTACGTCGCCACCACTTACTTCCCTCTCCTCCCTCACCCTCT 100
    ||||||||||||||||||||||||||||||||||||||||||||||||||
 51 TGCTTCTACTACGTCGCCACCACTTACTTCCCTCTCCTCCCTCACCCTCT 100

101 CTCCTACTTCGCCTGGCCTCTCTACTGGGCCTGCCAGGGCTGCGTCCTAA 150
    ||||||||||||||||||||||||||||||||||||||||||||||||||
101 CTCCTACTTCGCCTGGCCTCTCTACTGGGCCTGCCAGGGCTGCGTCCTAA 150

151 CCGGCGTCTGGGTCATAGCCCACGAGTGCGGCCACCACGCCTTCAGCGAC 200
    ||||||||||||||||||||||||||||||||||||||||||||||||||
151 CCGGCGTCTGGGTCATAGCCCACGAGTGCGGCCACCACGCCTTCAGCGAC 200

201 TACCAGTGGCTGGACGACACCGTCGGCCTCATCTTCCACTCCTTCCTCCT 250
    ||||||||||||||||||||||||||||||||||||||||||||||||||
201 TACCAGTGGCTGGACGACACCGTCGGCCTCATCTTCCACTCCTTCCTCCT 250

251 CGTCCCTTACTTCTCCTGGAAGTACAGTCATCGACGCCACCATTCCAACA 300
    ||||||||||||||||||||||||||||||||||||||||||||||||||
251 CGTCCCTTACTTCTCCTGGAAGTACAGTCATCGACGCCACCATTCCAACA 300

301 CTGGCTCCCTCGAGAGAGACGAAGTGTTTGTCCCCAAGAAGAAGTCAGAC 350
    ||||||||||||||||||||||||||||||||||||||||||||||||||
301 CTGGCTCCCTCGAGAGAGACGAAGTGTTTGTCCCCAAGAAGAAGTCAGAC 350
                                              . Forward  .
351 ATCAAGTGGTACGGCAAGTACCTCAACAACCCTTTGGGACGCACCGTGAT 400
    ||||||||||||||||||||||||||||||||||||||||||||||||||
351 ATCAAGTGGTACGGCAAGTACCTCAACAACCCTTTGGGACGCACCGTGAT 400
        primer  ▼       .         .         .         .
401 GTTAACGGTTTAGTTCACTCTCGGCTGGCCTTTGTACTTAGCCTTCAACG 450
    ||||||||||  ||||||||||||||||||||||||||||||||||||||
401 GTTAACGGTTCAGTTCACTCTCGGCTGGCCTTTGTACTTAGCCTTCAACG 450

451 TCTCGGGGAGACCTTACGACGGCGGCTTCGCTTGCCATTTCCACCCCAAC 500
    ||||||||||||||||||||||||||||||||||||||||||||||||||
451 TCTCGGGGAGACCTTACGACGGCGGCTTCGCTTGCCATTTCCACCCCAAC 500

501 GCTCCCATCTACAACGACCGTGAGCGTCTCCAGATATACATCTCCGACGC 550
    ||||||||||||||||||||||||||||||||||||||||||||||||||
501 GCTCCCATCTACAACGACCGTGAGCGTCTCCAGATATACATCTCCGACGC 550

551 TGGCATCCTCGCCGTCTGCTACGGTCTCTACCGCTACGCTGCTGTCCAAG 600
    ||||||||||||||||||||||||||||||||||||||||||||||||||
551 TGGCATCCTCGCCGTCTGCTACGGTCTCTACCGCTACGCTGCTGTCCAAG 600

601 GAGTTGCCTCGATGGTCTGCTTCTACGGAGTTCCTCTTCTGATTGTCAAC 650
    ||||||||||||||||||||||||||||||||||||||||||||||||||
601 GAGTTGCCTCGATGGTCTGCTTCTACGGAGTTCCTCTTCTGATTGTCAAC 650

651 GGGTTCTTAGTTTTGATCACTTACTTGCAGCACACGCATCCTTCCCTGCC 700
    ||||||||||||||||||||||||||||||||||||||||||||||||||
651 GGGTTCTTAGTTTTGATCACTTACTTGCAGCACACGCATCCTTCCCTGCC 700

701 TCACTATGACTCGTCTGAGTGGGATTGGTTGAGGGGAGCTTTGGCCACCG 750
    ||||||||||||||||||||||||||||||||||||||||||||||||||
701 TCACTATGACTCGTCTGAGTGGGATTGGTTGAGGGGAGCTTTGGCCACCG 750

751 TTGACAGAGACTACGGAATCTTGAACAAGGTCTTCCACAATATCACGGAC 800
    ||||||||||||||||||||||||||||||||||||||||||||||||||
751 TTGACAGAGACTACGGAATCTTGAACAAGGTCTTCCACAATATCACGGAC 800
       Reverse primer
801 ACGCACGTGGCGCATCACCTGTTCTCGACCATGCCGCATTATCATGCGAT 850
    ◄─────────────────────
    ||||||||||||||||||||||||||||||||||||||||||||||||||
801 ACGCACGTGGCGCATCACCTGTTCTCGACCATGCCGCATTATCATGCGAT 850

851 GGAAGCTACGAAGGCGATAAAGCCGATACTGGGAGAGTATTATCAGTTCG 900
    ||||||||||||||||||||||||||||||||||||||||||||||||||
851 GGAAGCTACGAAGGCGATAAAGCCGATACTGGGAGAGTATTATCAGTTCG 900

901 ATGGGACGCCGGTGGTTAAGGCGATGTGGAGGGAGGCGAAGGAGTGTATC 950
    ||||||||||||||||||||||||||||||||||||||||||||||||||
901 ATGGGACGCCGGTGGTTAAGGCGATGTGGAGGGAGGCGAAGGAGTGTATC 950

951 TATGTGGAACCGGACAGGGAAGGTGACAAGAAAGG 985
    |||||||||||||||||||||||||||||||||||
951 TATGTGGAACCGGACAGGGAAGGTGACAAGAAAGG 985

FIG. 1B

```
              1                                                              50
DMS100        ---------- ---------- ---------- ---------- --------IP
Quantum       ---------- ---------- ---------- ---------- --------IP
Bnfad2        MGAGGRMQVS PPSKKSETDT IKRVPCETPP FTVGELKKAI PPHCFKRSIP 51                                                            100
DMS100        RSFSYLIWDI IIASCFYYVA TTYFPLLPHP LSYFAWPLYW ACQGCVLTGV
Quantum       RSFSYLIWDI IIASCFYYVA TTYFPLLPHP LSYFAWPLYW ACQGCVLTGV
Bnfad2        RSFSYLIWDI IIASCFYYVA TTYFPLLPHP LSYFAWPLYW ACQGCVLTGV 101                                                           150
DMS100        WVIAHECGHH AFSDYQWLDD TVGLIFHSFL LVPYFSWKYS HRRHHSNTGS
Quantum       WVIAHECGHH AFSDYQWLDD TVGLIFHSFL LVPYFSWKYS HRRHHSNTGS
Bnfad2        WVIAHECGHH AFSDYQWLDD TVGLIFHSFL LVPYFSWKYS HRRHHSNTGS 151                                      ▼                    200
DMS100        LERDEVFVPK KKSDIKWYGK YLNNPLGRTV MLTV*----- ----------
Quantum       LERDEVFVPK KKSDIKWYGK YLNNPLGRTV MLTVQFTLGW PLYLAFNVSG
BNfad2        LERDEVFVPK KKSDIKWYGK YLNNPLGRTV MLTVQFTLGW PLYLAFNVSG 201                                                           250
DMS100        ---------- ---------- ---------- ---------- ----------
Quantum       RPYDGGFACH FHPNAPIYND RERLQIYISD AGILAVCYGL YRYAAVQGVA
BNfad2        RPYDGGFACH FHPNAPIYND RERLQIYISD AGILAVCYGL FRYAAAQGVA 251                                                           300
DMS100        ---------- ---------- ---------- ---------- ----------
Quantum       SMVCFYGVPL LIVNGFLVLI TYLQHTHPSL PHYDSSEWDW LRGALATVDR
BNfad2        SMVCFYGVPL LIVNGLLVLI TYLQHTHPSL PHYDSSEWDW LRGALATVDR 301                                                           350
DMS100        ---------- ---------- ---------- ---------- ----------
Quantum       DYGILNKVFH NITDTHVAHH LFSTMPHYHA MEATKAIKPI LGEYYQFDGT
BNfad2        DYGILNKVFH NITDTHVAHH LFSTMPHYHA MEATKAIKPI LGEYYQFDGT 351                              384
DMS100        ---------- ---------- ---------- ----
Quantum       PVVKAMWREA KECIYVEPDR EGDKK----- ----
BNfad2        PVVKAMWREA KECIYVEPDR QGEKKGVFWY NNKL
```

FIG. 2

```
        Forward primer
   1 CAAGAATTTGTCCCACAGTACACGGATGCTCAGATACACTGTCCCTCTCC  50
     ||||||||||||||||||||||||||||||||||||||||||||||||||
   1 CAAGAATTTGTCCCACAGTACACGGATGCTCAGATACACTGTCCCTCTCC  50   Exon 4

51 CCATGCTCGCTTACCCTCTCTATCTGGTAAATCCTAATTCCTAATTTTTC 100
     ||||||||||||||||||||||||||||||||||||||||||||||||||
  51 CCATGCTCGCTTACCCTCTCTATCTGGTAAATCCTAATTCCTAATTTTTC 100

101 TTCCTGATTATAATTACAATTTTGAATTTTTAGATTTTGAGTATTAACTA 150   Intron 4
     ||||||||||||||||||||||||||||||||||||||||||||||||||
 101 TTCCTGATTATAATTACAATTTTGAATTTTTAGATTTTGAGTATTAACTA 150

151 AATATAAATTAAATTTGTTTGGGGATGACTACAGTGGTACAGAAGTCCTG 200
     ||||||||||||||||||||||||||||||||||||||||||||||||||
 151 AATATAAATTAAATTTGTTTGGGGATGACTACAGTGGTACAGAAGTCCTG 200

201 GTAAAGAAGGGTCACATTATAACCCATACAGTAGTTTATTTGCCCCAAGC 250
     ||||||||||||||||||||||||||||||||||||||||||||||||||
 201 GTAAAGAAGGGTCACATTATAACCCATACAGTAGTTTATTTGCCCCAAGC 250

251 GAGAGAAAGCTTATTGCAACTTCAACTACTTGCTGGTCGATCGTGTTGGC 300   Exon 5
     ||||||||||||||||||||||||||||||||||||||||||||||||||
 251 GAGAGAAAGCTTATTGCAACTTCAACTACTTGCTGGTCGATCGTGTTGGC 300

301 CACTCTTGTTTATCTATCATTCCTCGTTGGTCCAGTCACAGTTCTAAAAG 350
     ||||||||||||||||||||||||||||||||||||||||||||||||||
 301 CACTCTTGTTTATCTATCATTCCTCGTTGGTCCAGTCACAGTTCTAAAAG 350

351 TCTATGGTGTTCCTTACATTGTAAGTTTCATATATTTCTTTATTATATCA 400
     ||||||||||||||||||||||||||||||||||||||||||||||||||
 351 TCTATGGTGTTCCTTACATTGTAAGTTTCATATATTTCTTTATTATATCA 400   Intron 5

401 TTGCTAATATAATTTGTTTTTGACATAAAAGTTTTGGAAAAATTTCAGAT 450
     ||||||||||||||||||||||||||||||||||||||||||||||||||
 401 TTGCTAATATAATTTGTTTTTGACATAAAAGTTTTGGAAAAATTTCAGAT 450

451 CTTTGTAATGTGGTTGGACGCTGTCACGTACTTGCATCATCATGGTCACG 500
     ||||||||||||||||||||||||||||||||||||||||||||||||||
 451 CTTTGTAATGTGGTTGGACGCTGTCACGTACTTGCATCATCATGGTCACG 500   Exon 6
                                      ▼ Reverse primer
 501 ATGATAAGCTGCCTTGGTACAGAGGCAAGATAAGTAGATCAACATTATTT 550
     ||||||||||||||||||||||||||||||||||||||||||||||||||
 501 ATGATAAGCTGCCTTGGTACAGAGGCAAGGTAAGTAGATCAACATTATTT 550

551 ATAAGAAGCAATAATGATTAGTAGTTGAATAATCTGAATTTTTGATGTTT 600   Intron 6
     ||||||||||||||||||||||||||||||||||||||||||||||||||
 551 ATAAGAAGCAATAATGATTAGTAGTTGAATAATCTGAATTTTTGATGTTT 600

601 TTGTACAATAATAGGAATGGAGTTATTTACGTGGAGGATTAACAACAGTT 650   Exon 7
     ||||||||||||||||||||||||||||||||||||||||||||||||||
 601 TTGTACAATAATAGGAATGGAGTTATTTACGTGGAGGATTAACAACAGTT 650

Table 1.

| Marker | Trait | No. of Lines tested | | Average fatty acid content | | t-value |
|---|---|---|---|---|---|---|
| | | With marker | Without marker | With marker | Without marker | |
| FAD2GM | C18:1 | 85 | 98 | 75.67 | 64.23 | 15.49** |
| FAD3cGM | C18:3 | 74 | 99 | 2.81 | 5.42 | 13.13** |

** significant at $t = 0.01$.

HO/LL CANOLA WITH RESISTANCE TO CLUBROOT DISEASE

CROSS-REFERENCE TO RELATED APPLICATIONS

This application is a continuation-in-part of U.S. patent application Ser. No. 13/024,232, filed Feb. 2, 2011, now abandoned.

FIELD OF THE DISCLOSURE

The present disclosure relates to plants resistant to diseases, for example, to *Brassica napus* plants resistant to the disease, clubroot. The present disclosure also relates to molecular markers that are linked to clubroot disease resistance. In particular embodiments, the disclosure relates to compositions and methods for introducing clubroot disease resistance into a plant, for example, by using molecular markers linked to clubroot disease resistance. Particular embodiments relate to methods for using particular nucleic acid sequences to identify plants that are likely to have a clubroot disease resistance phenotype.

BACKGROUND

Clubroot is a widespread disease that causes serious problems in many *Brassica* growing areas. See, e.g., Dixon (1999) Grower April 29:28-9. The disease is caused by *Plasmodiophora brassicae*, a unicellular organism. Symptoms of the disease include root malformations with hard swellings (clubs) that eventually rot. The disease also causes stunting through reduced growth, and wilting of leaves is observed under water stress. Chemical control of the disease is not effective.

The genus of the *Brassica* comprises several species of commercial interest, such as *B. rapa* (e.g., Chinese cabbage, pak choi, turnip); *B. napus* (e.g., oil seed, swede); *B. juncea* (e.g., mustard); *B. nigra* (e.g., black mustard); and *B. oleracea* (e.g., cauliflower, broccoli, cabbage, Brussels sprouts, savoy cabbage, borecole, kohl rabi, borecole, etc.). While subspecies within a species of the *Brassica* genus are usually sexually compatible, this is not necessarily the case between different species of the *Brassica* genus. For example, *B. rapa* and *B. oleracea* do not have the same number of chromosomes (10 chromosomes versus 9 chromosomes), and are therefore not sexually compatible. This renders the transfer of a trait from one *Brassica* species to another particularly difficult.

Several sources of resistance to clubroot have been described within the *Brassica* genus. See, e.g., Bradshaw et al. (1997) Ann. Appl. Biol. 130:337-48; Gowers (1982) Euphytica 31:971-6. Some resistances are monogenic, some polygenic, some are dominant, and some are recessive. Monogenic dominant resistances have been described in *B. rapa* and *B. napus*, such as, for example, a monogenic dominant resistance in the *B. rapa* Chinese cabbage. Yoshikawa (1983) Japan Agricultural Research Quarterly 17(1):6-11. Chinese cabbage $F_1$-hybrids with this resistance have been shown to have good protection against clubroot, although a small number of strains ('races') of clubroot have been able to break through this resistance.

Clubroot disease infection is considered to be a major threat to the canola cultivation industry. Attempts to breed for clubroot resistant canola varieties will produce significant number of segregating plants that need to be screened for clubroot disease resistance. The current practice of screening breeding materials for clubroot disease resistance includes phenotyping individual plants through observation of that plant's phenotypic reaction after inoculation of the plant with the *P. brassicae* pathogen. This already cumbersome and time-consuming process is further complicated by current regulatory restrictions on the transport of clubroot pathogen or any infected materials. The foregoing considerations make the cost of screening breeding materials for clubroot disease resistance extremely high, and also significantly hinder breeding efforts by limiting the number of lines that may be tested at one time.

BRIEF SUMMARY OF THE DISCLOSURE

Described herein are a *Brassica* spp. plant, and parts thereof, wherein the plant comprises at least one trait selected from the group consisting of: high oleic and/or low linolenic acid content; resistance to *Plasmodiophora brassicae*; resistance to a herbicide (e.g., glyphosate or an imidazolinone herbicide); and restorer of cytoplasmic male sterility. In some embodiments, the *Brassica* spp. plant is selected from the group consisting of *B. rapa, B. napus, B. juncea, B. nigra*, and *B. oleracea*. For example, in particular embodiments utilitze *B. napus*. Particular embodiments provide a *Brassica* spp. plant, and parts thereof, wherein the plant evidences high oleic and/or low linolenic acid content compared to a wild-type plant of the same species, evidences resistance to *Plasmodiophora brassicae* compared to a wild-type plant of the same species, displays resistance to an imidazolinone compared to a wild-type plant of the same species, and comprises a cytoplasmic male sterility system restorer gene. Particular embodiments may include a method of growing a *Brassica* spp. plant, or parts thereof, according to the invention, in a field comprising *P. brassicae*.

In particular embodiments, the plant (or parts thereof) may comprise a genome, homozygous with respect to genetic alleles that are native to a first parent and normative to a second parent of the plant, wherein the second parent evidences significantly less oleic and/or higher linolenic acid content than the first parent. In some examples, the plant (or parts thereof) comprises alleles from the first parent in a hybrid or inbred combination in at least one locus selected from a locus mapping to a linkage group selected from the group consisting of N14, N4, N5 and N1 of a *Brassica* species. In particular examples, the allele from the first parent may be mapped by one or more of the markers set forth as SEQ ID NOs:5, 6, 14, and 15.

Also described herein are nucleic acid molecular markers that are linked (e.g., linked; tightly linked; or extremely tightly linked) to a high oleic acid (HO) and/or low linolenic acid (LL) phenotype in *Brassica napus*. In particular embodiments, a marker that is linked to a HO phenotype is linked to a mutation in a fad2 gene. In particular embodiments, a marker that is linked to a LL phenotype is linked to a mutation in a fad3 gene. In some embodiments, markers that are linked to a HO/LL phenotype in *B. napus* may be used to introduce the HO/LL phenotype into other plants (e.g., other *Brassica* species). Some embodiments include methods of using at least one nucleic acid molecular marker that is linked to a HO/LL phenotype in *B. napus*, for example and without limitation, to identify plants with a HO/LL phenotype; and/or to introduce a HO/LL phenotype to new plant genotypes and germplasms (e.g., through marker-assisted breeding or genetic transformation).

Further described are means for introducing a HO phenotype into a plant of the genus, *Brassica*, and means for introducing a LL phenotype into a plant of the genus, *Brassica*. In some examples, a means for introducing a HO phenotype into a plant of the genus, *Brassica*, is a "C" to "T" mutation at position 411 in the fad2 gene in a *B. napus* plant. In some examples, a means for introducing a LL phenotype into a plant of the genus, *Brassica*, is a "G" to "A" mutation at the first base of a 5' splice site of the third intron in the fad32 gene in a *B. napus* plant.

Also described are means for identifying a plant carrying a gene contributing to a HO phenotype in a plant of the genus, *Brassica*. In some examples, a means for identifying a plant carrying a gene contributing to a HO phenotype is a probe that specifically hybridizes to a segment of the *B. napus* fad2 gene comprising a "C" to "T" mutation at position 411, but does not hybridize to the same segment of a wild-type *B. napus* fad2 gene without this mutation. Also described are means for identifying a plant carrying a gene contributing to a LL phenotype in a plant of the genus, *Brassica*. In some examples, a means for identifying a plant carrying a gene contributing to a LL phenotype is a probe that specifically hybridizes to a segment of the *B. napus* fad32 gene comprising a "G" to "A" mutation at the first base of a 5' splice site of the third intron, but does not hybridize to the same segment of a wild-type *B. napus* fad32 gene without this mutation.

In some embodiments, a seed of a *Brassica* spp. plant of the invention may comprise at least 63% oleic acid (C18:1). For example, a seed of the *Brassica* spp. plant of the invention may comprise at least 77% oleic acid (C18:1). In some embodiments of the invention, a seed of a *Brassica* spp. plant may comprise not more than 6% linolenic acid (C18:3). For example, a seed of the *Brassica* spp. plant may comprise not more than 1.5% linolenic acid (C18:3).

In some embodiments, a plant of the invention (or part thereof) may comprise a nucleotide sequence that is specifically hybridizable to the complement of a nucleotide sequence selected from the group consisting of SEQ ID NOs:7 and 12. In these and further embodiments, the plant, or parts thereof, may be resistant to an imidazolinone (for example, an imidizolinone selected from the group consisting of imazamethbenz, imazamox, imazapic, imazapyr, imazaquin, and imazethapyr). Particular embodiments include a method of controlling at least one weed in a field, wherein the field contains at least one *Brassica* spp. plant, or parts thereof, and applying an imidazolinone to at least a portion of the field.

Also described herein are nucleic acid molecular markers that are linked (e.g., linked; tightly linked; or extremely tightly linked) to a clubroot disease resistance phenotype in *Brassica napus*. In some embodiments, markers that are linked to a clubroot disease resistance phenotype in *B. napus* may be used to introduce the clubroot disease resistance phenotype into other plants (e.g., other *Brassica* species). Some embodiments include methods of using at least one nucleic acid molecular marker that is linked to a clubroot disease resistance phenotype in *B. napus*, for example and without limitation, to identify plants with a clubroot disease resistance phenotype; and/or to introduce a clubroot disease resistance phenotype to new plant genotypes (e.g., through marker-assisted breeding or genetic transformation). In particular examples, a marker that is linked to clubroot disease resistance may be determined and/or identified by DNA amplification utilizing a primer selected from the group consisting of SEQ ID NOs:18-22, or a functional equivalent thereof.

Further described are means for introducing clubroot disease resistance into a *Brassica* spp. plant, and means for identifying a plant carrying a gene contributing to clubroot disease resistance. In some examples, a means for introducing a clubroot disease resistance into a *Brassica* spp. plant is a contiguous segment of genomic DNA that is 300 bp in length and is amplified by the exemplary primers of SEQ ID NOs:18 and 19, which marker is linked to clubroot disease resistance in a *B. napus* plant. Also described are means for identifying a plant carrying a gene contributing to clubroot disease resistance. In some examples, a means for identifying a plant carrying a gene contributing to clubroot disease resistance is a probe that specifically hybridizes to a contiguous segment of genomic DNA that is 300 bp in length and is amplified by the exemplary primers of SEQ ID NOs:18 and 19.

The foregoing and other features will become more apparent from the following detailed description of several embodiments, which proceeds with reference to the accompanying figures.

BRIEF DESCRIPTION OF THE FIGURES

FIG. 1 includes partial genomic nucleotide sequences of the fad2 gene cloned from *B. napus* varieties, DMS100 and Quantum. The top shows the partial genomic nucleotide sequence of the fad2 gene cloned from DMS100 (SEQ ID NO:7), and the bottom shows sequence the partial genomic nucleotide sequence of the fad2 gene cloned from Quantum (SEQ ID NO:9). The arrowhead indicates a single nucleotide mutation of "C" to "T," which resulted in a stop codon ("TAG") (shaded). The mutant allele-specific forward (SEQ ID NO:5) and reverse (SEQ ID NO:6) primers for PCR-based identification of a mutant allele-specific marker are shown in bold font and underlined.

FIG. 2 includes amino acid sequences of the fad2 gene, degenerated from the genomic nucleotide sequence cloned from DMS100 (SEQ ID NO:8), Quantum (SEQ ID NO:10), and from a published *Brassica napus* fad2 gene (BNfad2) (SEQ ID NO:11). The arrowhead indicates the position of the stop codon resulting from a single nucleotide mutation ("C" to "T") in DMS100.

FIG. 3 includes genomic nucleotide sequences of the fad3c gene cloned from DMS100 and Quantum. The top shows the fad3c gene cloned from DMS100 (SEQ ID NO:12), and the bottom shows the fad3c gene cloned from Quantum (SEQ ID NO:13). The exons corresponding to exons 4, 5, 6 and 7 of the fad3 gene in *Brassica rapa* and *Arabidopsis* are boxed, and the introns corresponding to and introns 4, 5 and 6 of the fad3 gene in *Brassica rapa* and *Arabidopsis* are unboxed. The arrowhead indicates a single nucleotide mutation of "G" to "A." The forward (SEQ ID NO:14) and mutant allele-specific reverse (SEQ ID NO:15) primers for PCR-based identification of a mutant allele-specific marker are shown in bold font and underlined.

SEQUENCE LISTING

Figure 4:
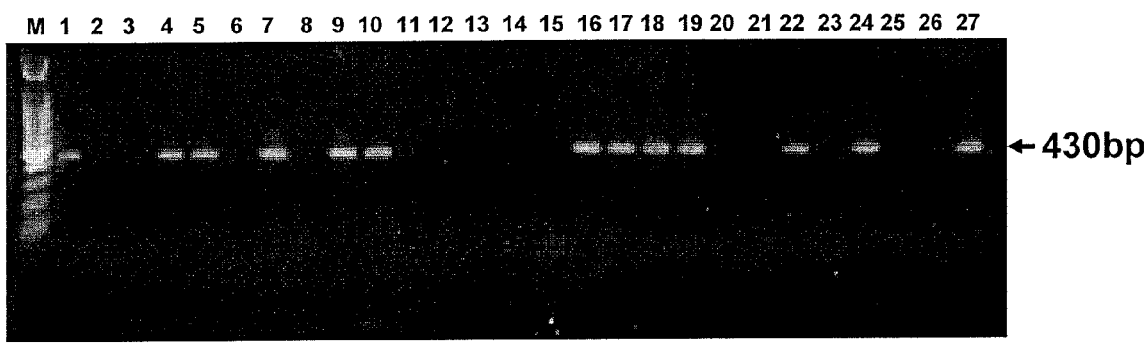
FIG. 4 includes a table that correlates the mutant allele-specific markers and fatty acid content of 184 doubled haploid (DH) lines derived from a cross of Quantum and DMS100 (top), as well as electrophoresis results of PCR products amplified from the mutant allele-specific marker for the fad2 gene (bottom).

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand is understood to be included by any reference to the displayed strand.

SEQ ID NOs:1-2 are primers used to amplify a fad2 gene from genomic *B. napus* DNA of parental lines, DMS100 and Quantum.

SEQ ID NOs:3-4 are primers used to amplify a fad31 gene from genomic *B. napus* DNA of parental lines, DMS100 and Quantum.

SEQ ID NO:5 is a mutant-specific forward primer for identifying and/or determining a fad2 allele that contributes to high oleic and/or low linoleic acid content in *Brassica*.

SEQ ID NO:6 is a reverse primer for identifying and/or determining a fad2 allele that contributes to high oleic and/or low linoleic acid content in *Brassica*.

SEQ ID NO:7 is a partial genomic nucleotide sequence of the fad2 gene cloned from *B. napus* variety, DMS100.

SEQ ID NO:8 is an amino acid sequence of the fad2 gene product, degenerated from the genomic nucleotide sequence cloned from *B. napus* variety, DMS100, which sequence is interrupted by a "STOP" codon as indicated.

SEQ ID NO:9 is a partial genomic nucleotide sequence of the fad2 gene cloned from *B. napus* variety, Quantum.

SEQ ID NO:10 is an amino acid sequence of the fad2 gene product, degenerated from the genomic nucleotide sequence cloned from *B. napus* variety, Quantum.

SEQ ID NO:11 is an amino acid sequence of the fad2 gene product, degenerated from a genomic nucleotide sequence from *B. napus* variety, BNfad2.

SEQ ID NO:12 is a genomic nucleotide sequence of the fad3c gene cloned from *B. napus* variety, DMS100.

SEQ ID NO:13 is a genomic nucleotide sequence of the fad3c gene cloned from *B. napus* variety, Quantum.

SEQ ID NOs:14 is a forward primer for identifying and/or determining a fad32 allele that contributes to high oleic and/or low linoleic acid content in *Brassica*.

SEQ ID NO:15 is a mutant-specific reverse primer for identifying and/or determining a fad32 allele that contributes to high oleic and/or low linoleic acid content in *Brassica*.

SEQ ID NOs:16 and 17 are the primers used to amplify a fad32 gene from genomic *B. napus* DNA of parental lines, DMS100 and Quantum.

SEQ ID NOs:18-21 are exemplary primer sequences useful for identifying and/or determining a marker for clubroot disease resistance.

SEQ ID NOs:22 is the fluorescently-labeled M13 universal primer sequence used to amplify labeled DNA fragments when used with SEQ ID NOs:20 and 21, for detection.

DETAILED DESCRIPTION

I. Overview of Several Embodiments

Described herein are *Brassica* spp. (e.g., *B. napus*) plants and progeny thereof comprising a clubroot disease resistance phenotype. Also described herein are plant parts obtained from such a *Brassica* plant, including seeds and plant materials of the plant. In particular embodiments, the resistance to clubroot may be monogenic and/or multigenic. In particular embodiments, the resistance to clubroot may be dominant and/or recessive.

Using a *Brassica napus* plant comprising a clubroot disease resistance phenotype, molecular markers that are tightly linked to the clubroot disease resistance phenotype have been identified. In particular, one Simple Sequence Repeat (SSR) marker locus was identified that is tightly linked with the clubroot disease resistance phenotype. This SSR marker may be particularly useful for introducing this phenotype into other plants (e.g., other *B. napus* varieties, and other *Brassica* species), for example, through traditional plant breeding, and also for identifying plants likely to have this phenotype (e.g., among plants generated by recombinant genetic engineering). Utilization of at least one molecular marker that is tightly linked to the clubroot disease resistance phenotype in a *Brassica* breeding program may greatly reduce the time and cost of screening breeding materials for clubroot disease resistance. For example, utilizing such a marker may reduce the need for expensive clubroot disease resistance screening, thereby significantly facilitating the breeding of clubroot disease resistant canola varieties.

II. Terms

Backcrossing: Backcrossing methods may be used to introduce a nucleic acid sequence into plants. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Clubroot resistance: Resistance or tolerance of a plant to clubroot refers to increased growth, productivity, and/or reduction in root nodule size and/or number in the plant compared to a non-resistant and/or non-tolerant strain of the same plant when grown in a field comprising *Plasmodiophora brassicae*. As used herein, clubroot resistance also includes tolerance to clubroot. Clubroot resistance may be conferred by one or more genes, alleles, or events.

Genetic locus: As used herein, the term, "genetic locus," refers to a location on a chromosome.

Genomic locus: As used herein, the term, "genomic locus," refers to a location within the entire set of chromosomes of an organism.

Linkage disequilibrium: As used herein, the term "linkage disequilibrium" refers to a statistical association between two loci or between a trait and a marker.

Linked, tightly linked, and extremely tightly linked: As used herein, linkage between genes or markers refers to the phenomenon in which genes or markers on a chromosome show a measurable probability of being passed on together to individuals in the next generation. The closer two genes or markers are to each other, the closer to (1) this probability becomes. Thus, the term "linked" may refer to one or more genes or markers that are passed together with a gene with a probability greater than 0.5 (which is expected from independent assortment where markers/genes are located on different chromosomes). Because the proximity of two genes or markers on a chromosome is directly related to the probability that the genes or markers will be passed together to individuals in the next generation, the term "linked" may also refer herein to one or more genes or markers that are located within about 2.0 Mb of one another on the same *Brassica* spp. chromosome. Thus, two "linked" genes or markers may be separated by about 2.1 Mb; 2.00 Mb; about 1.95 Mb; about 1.90 Mb; about 1.85 Mb; about 1.80 Mb; about 1.75 Mb; about 1.70 Mb; about 1.65 Mb; about 1.60 Mb; about 1.55 Mb; about 1.50 Mb; about 1.45 Mb; about 1.40 Mb; about 1.35 Mb; about 1.30 Mb; about 1.25 Mb; about 1.20 Mb; about 1.15 Mb; about 1.10 Mb; about 1.05 Mb; about 1.00 Mb; about 0.95 Mb; about 0.90 Mb; about 0.85 Mb; about 0.80 Mb; about 0.75 Mb; about 0.70 Mb; about 0.65 Mb; about 0.60 Mb; about 0.55 Mb; about 0.50 Mb; about 0.45 Mb; about 0.40 Mb; about 0.35 Mb; about 0.30 Mb; about 0.25 Mb; about 0.20 Mb; about 0.15 Mb; about 0.10 Mb; about 0.05 Mb; about 0.025 Mb; about 0.012 Mb; and about 0.01 Mb. A gene may be "linked" to a marker that resides within an exon or intron of the gene. In this case, the separation between the linked gene and marker is 0.00 Mb.

Particular examples of markers that are "linked" to fad2 include nucleotide sequences in linkage group N5 and N1 of the *B. napus* genome, e.g., a "C" to "T" mutation at position 411 in the *B. napus* fad2 gene. Particular examples of markers that are "linked" to fad3 include nucleotide sequences in linkage group N14 and N4 of the *B. napus* genome, e.g., a "G" to "A" mutation at the first base of a 5' splice site of the third intron in the *B. napus* fad32 gene.

Markers and/or genes may also be "linked" to a phenotype, for example, a phenotype in which the linked gene or gene linked to the linked marker is involved. Some embodiments include markers that are linked to HO, LL, imidazolinone resistance, and/or clubroot disease resistance phenotypes. Particular examples of markers that are "linked" to HO/LL phenotypes include markers that are linked to fad2 and fad3. Particular examples of markers that are "linked" to a clubroot disease resistance phenotype include a contiguous segment of genomic DNA that is 300 bp in length and is amplified by the exemplary primers of SEQ ID NOs:16 and 17. As will be understood by those of skill in the art, the length of this SSR marker will vary if nucleotides are added or subtracted from the span of genomic DNA located between the distal ends of the particular primers used when annealed.

As used herein, the term "tightly linked" may refer to one or more genes or markers that are located within about 0.5 Mb of one another on the same chromosome. Thus, two "tightly linked" genes or markers may be separated by about 0.6 Mb; about 0.55 Mb; 0.5 Mb; about 0.45 Mb; about 0.4 Mb; about 0.35 Mb; about 0.3 Mb; about 0.25 Mb; about 0.2 Mb; about 0.15 Mb; about 0.12 Mb; about 0.1 Mb; about 0.05 Mb; and about 0.00 Mb. Particular examples of markers that are "tightly linked" to fad2 include certain nucleotide sequences in linkage group N5 and N1 of the *B. napus* genome, e.g., a "C" to "T" mutation at position 411 in the *B. napus* fad2 gene. Particular examples of markers that are "tightly linked" to fad3 include certain nucleotide sequences in linkage group N14 and N4 of the *B. napus* genome, e.g., a "G" to "A" mutation at the first base of a 5' splice site of the third intron in the *B. napus* fad32 gene. Particular examples of markers that are "tightly linked" to a clubroot disease resistance phenotype include a contiguous segment of genomic DNA that is 300 bp in length and is amplified by the exemplary primers of SEQ ID NOs:16 and 17.

As used herein, the term "extremely tightly linked" may refer to one or more genes or markers that are located within about 100 kb of one another on the same chromosome. Thus, two "extremely tightly linked" genes or markers may be separated by about 125 kb; about 120 kb; about 115 kb; about 110 kb; about 105 kb; 100 kb; about 95 kb; about 90 kb; about 85 kb; about 80 kb; about 75 kb; about 70 kb; about 65 kb; about 60 kb; about 55 kb; about 50 kb; about 45 kb; about 40 kb; about 35 kb; about 30 kb; about 25 kb; about 20 kb; about 15 kb; about 12 kb; about 10 kb; about 5 kb; about 1 kb; and about 0 kb. Particular examples of markers that are "extremely tightly linked" to fad2 include certain nucleotide sequences in linkage group N5 and N1 of the *B. napus* genome, e.g., a "C" to "T" mutation at position 411 in the *B. napus* fad2 gene. Particular examples of markers that are "extremely tightly linked" to fad3 include certain nucleotide sequences in linkage group N14 and N4 of the *B. napus* genome, e.g., a "G" to "A" mutation at the first base of a 5' splice site of the third intron in the *B. napus* fad32 gene. Particular examples of markers that are "extremely tightly linked" to a clubroot disease resistance phenotype include a contiguous segment of genomic DNA that is 300 bp in length and is amplified by the exemplary primers of SEQ ID NOs:16 and 17.

Linked, tightly linked, and extremely tightly genetic markers may be useful in marker-assisted breeding programs to identify individuals comprising linked phenotypes and/or gene types, and to breed these traits and/or genes into *Brassica* varieties.

Locus: As used herein, the term "locus" refers to a position on the genome that corresponds to a measurable characteristic (e.g., a trait). An SNP locus is defined by a probe that hybridizes to DNA contained within the locus.

Marker: As used herein, a marker refers to a gene or nucleotide sequence that can be used to identify plants having a particular allele, e.g., fad2, fad32, and a contiguous segment of genomic DNA that is 300 bp in length and is amplified by the exemplary primers of SEQ ID NOs:16 and 17. A marker may be described as a variation at a given genomic locus. A genetic marker may be a short DNA sequence, such as a sequence surrounding a single base-pair change (single nucleotide polymorphism, or "SNP"), or a long one, for example, a minisatellite/simple sequence repeat ("SSR"). A "marker allele" refers to the version of the marker that is present in a particular plant. As used herein, "marker" includes reference to a locus on a chromosome that serves to identify a unique position on the chromosome. A genotype may be defined by use of one or a plurality of markers. Thus, "marker" includes reference to one or more nucleotide position(s) in a gene located on a chromosome of a genome.

Molecular markers are particularly useful for accelerating the process of introducing a gene or quantitative trait loci (QTL) into an elite cultivar or breeding line via backcrossing. Markers linked to the gene can be used to select plants possessing the desired trait, and markers throughout the genome can be used to select plants that are genetically similar to the recurrent parent. Young and Tanksley (1989) Theor. Appl. Genet. 77:95-101; Hospital et al. (1992) Genetics 132:1199-210.

The term "marker," as used herein, may refer to a cloned segment of *Brassica* chromosomal DNA (for example, a segment of either the nucleotide sequence of SEQ ID NO:7 or SEQ ID NO:12), and may also or alternatively refer to a DNA molecule that is complementary to a cloned segment of *Brassica* chromosomal DNA.

Some embodiments include a "derivative" of a marker. As used herein, the term "derivative" may refer to a modification of a particular marker sequence. Illustrative of such modifications with regard to molecular markers are the substitution, insertion, and/or deletion of one or more bases relating to a nucleic acid sequence of a marker disclosed herein that preserve, slightly alter, or increase the function of the molecular marker in identifying one or more trait(s) (e.g., clubroot disease resistance, and high oleic and/or low linolenic traits in *Brassica* or other oil seed crop species). Such derivatives can be readily determined by one skilled in the art, for example, by using computer modeling techniques for predicting and optimizing sequence structure. The term "derivative" thus includes nucleic acid sequences that are substantially identical to one or more of the disclosed marker sequences herein, such that the derivative markers are able to possess the disclosed functionalities for use in marker-assisted breeding.

Marker-assisted breeding: As used herein, the term "marker-assisted breeding" may refer to an approach to breeding directly for one or more complex traits (e.g., HO, LL, imidazolinone resistance, and/or clubroot disease resistance). In current practice, plant breeders attempt to identify easily detectable traits, such as flower color, seed coat appearance, or isozyme variants, that are linked to an agronomically desired trait. The plant breeders then follow the agronomic trait in the segregating, breeding populations by following the segregation of the easily detectable trait. However, there are very few of these linkage relationships available for use in plant breeding.

Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electrophoretic techniques; the isozyme marker can be scored in seedling tissue, obviating the need to maintain plants to maturity; and co-dominance of the isozyme marker alleles allows discrimination between homozygotes and heterozygotes. See Rick (1983) in Tanksley and Orton, supra.

In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the *Brassica* genome. This is referred to herein as a "contiguous probe." The additional, contiguous nucleotide sequence is referred to as "upstream" or "downstream" of the original marker, depending on whether the contiguous nucleotide sequence from the *Brassica* chromosome is on the 5' or the 3' side of the original marker, as conventionally understood. For the example of markers linked to the HO trait, the additional, contiguous nucleotide sequence may be located between the original marker and position 411 of the fad2 gene on the *Brassica* chromosome. For the example of markers linked to the LL trait, the additional, contiguous nucleotide sequence may be located between the original marker and the first base of a 5' splice site of the third intron of a fad3 gene on the *Brassica* chromosome. As is recognized by those of ordinary skill in the art, the process of obtaining additional, contiguous nucleotide sequence for inclusion in a marker may be repeated nearly indefinitely (limited only by the length of the chromosome), thereby identifying additional markers along the *Brassica* chromosome. All above-described markers may be used in some embodiments of the present invention.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: radiolabeling by nick translation; random priming; tailing with terminal deoxytransferase; or the like, where the nucleotides employed are labeled, for example, with radioactive $^{32}$P. Other labels which may be used include, for example and without limitation: fluorophores; enzymes; enzyme substrates; enzyme cofactors; enzyme inhibitors; and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may contain a nucleotide sequence that is not contiguous to that of the original marker; this probe is referred to herein as a "noncontiguous probe." The sequence of the noncontiguous probe is located sufficiently close to the sequence of the original marker on the *Brassica* chromosome so that the noncontiguous probe is genetically linked to the same gene (e.g., fad2 or fad3). For example, in some embodiments, a noncontiguous probe can be located within 500 kb; 450 kb; 400 kb; 350 kb; 300 kb; 250 kb; 200 kb; 150 kb; 125 kb; 120 kb; 100 kb; 0.9 kb; 0.8 kb; 0.7 kb; 0.6 kb; 0.5 kb; 0.4 kb; 0.3 kb; 0.2 kb; or 0.1 kb of the original marker on the *Brassica* chromosome.

A probe may be an exact copy of a marker to be detected. A probe may also be a nucleic acid molecule comprising, or consisting of, a nucleotide sequence which is substantially identical to a cloned segment of *Brassica* chromosomal DNA (for example, as defined by a segment of SEQ ID NO:7 including nucleotide position 411, or a segment of SEQ ID NO:12 including the first nucleotide position of a 5' splice site of the third intron of the gene). As used herein, the term "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to the reference sequence.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. Thus, in some examples, a probe may be the complement of a DNA target. However, a nucleic acid molecule need not be 100% complementary to its target sequence to be specifically hybridizable. A nucleic acid molecule is specifically hybridizable when there is a sufficient degree of complementarity to avoid non-specific binding of the nucleic acid to all non-target sequences under conditions where specific binding is desired, for example, under stringent hybridization conditions. Thus, in some examples, a probe may be substantially identical to the complement of a DNA target. For example, a probe may be 85.5%; 86%; 87%; 88%; 89%; 90%; 91%; 92%; 93%; 94%; 95%; 96%; 97%; 98%; 99% or 99.5% identical to the complement of a DNA target.

A probe may be comprised within a nucleic acid molecule comprising additional nucleic acid sequences; for example, promoters; transcription signals; and/or vector sequences. A probe may be used to define additional markers that are tightly-linked to a gene involved in an HO, LL, imidazolinone resistance, and/or clubroot disease phenotype (e.g., fad2, and fad3). Markers thus identified may be equivalent to exemplary markers named in the present disclosure, and, thus, are within the scope of the invention.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, NY, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 25% mismatch between the hybridization molecule and the DNA target. "Stringent conditions" include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6× saline-sodium citrate (SSC) buffer, 5×Denhardt's solution, 0.5% SDS, and 100 µg sheared salmon testes DNA, followed by 15-30 minute sequential washes at 65° C. in 2×SSC buffer and 0.5% SDS, followed by 1×SSC buffer and 0.5% SDS, and finally 0.2×SSC buffer and 0.5% SDS.

Imidazolinone: As used herein, the term "imidazolinone" refers to an herbicide that interferes with the action of the enzyme, acetolactate synthase (ALS), also known as acetohydroxy acid synthase (AHAS), in a plant, which interference may eventually result in the death of the plant. Examples of imidazolinones include, but are not limited to: imazamethbenz; imazamox; imazapic; imazapyr; imazaquin; and imazethapyr.

As used herein, "imidazolinone resistance" refers to a phenotype characterized at least in part by a reduction, amelioration, and/or elimination of damage to the health and/or vitality of the resistant plant when compared to a wild-type plant of the same species. Imidazolinone resistance includes tolerance to imidazolinones. Imidazolinone resistance may be conferred by one or more genes, alleles, or events which alter acetolactate synthase (ALS), also known as acetohydroxy acid synthase (AHAS) that allow the enzyme to resist or tolerate the action of imidazolinones. Exemplary genes conferring imidazolinone resistance include, but are not limited to those described, for example, by Lee et al. (1988) EMBO J. 7:1241, and Miki et al. (1990) Theor. Appl. Genet. 80:449 (both of which are incorporated herein in their entirety by this reference). Resistance or tolerance of a plant to imidazolinone may allow imidazolinones to be used when needed to control weeds in an area in which the plant is cultivated.

InDel: As used herein, the term "InDel" is used generally to describe an insertion or a deletion in a gene. Thus, an "InDel" refers to a particular mutation that may be either an insertion, a deletion, or a combination thereof. An "insertion" or "addition," as used herein, refers to a change in an amino acid or nucleotide sequence resulting in the addition of one or more amino acid or nucleotide residues, respectively, as compared to the naturally occurring molecule.

Oil content: As used herein, "oil content" refers to a characterization of the oil in a plant or plant part (e.g., a seed). In some embodiments, oil content is expressed as a percent of the whole dried seed. In some embodiments, a particular seed oil content and is characteristic of a particular plant variety, and may be used to distinguish a plant of that particular variety from other plants of the same species. Oil content may be measured through the use of various analytical techniques, such as, for example and without limitation: NMR, NIR, FAME analysis, and Soxhlet extraction.

In particular embodiments, a characteristic oil content may include a description of a "percent oleic acid," and/or a "percent linolenic acid." As used herein, a "percent oleic acid" refers to the percent of the total seed oil that is oleic acid as determined by FAME analysis. As used herein, a "percent linolenic acid" refers to the percent of the total seed oil that is linolenic acid as determined by FAME analysis.

FAME analysis may be used to measure the percent composition of a particular fatty acid in the total fatty acids in a sample. With regard to seed oil, the percentage may be determined by extracting a sample of oil from the seed, producing the methyl esters of fatty acids present in that oil sample, and analyzing the proportions of the various fatty acids in the sample using gas chromatography. The oil content thus determined may be a distinguishing characteristic of a variety.

Sequence identity: The term "sequence identity" or "identity," as used herein in the context of two nucleic acid or polypeptide sequences, may refer to the residues in the two sequences that are the same when aligned for maximum correspondence over a specified comparison window.

When percentage of sequence identity is used in reference to proteins, it is recognized that residue positions which are not identical often differ by conservative amino acid substitutions, where amino acid residues are substituted for other amino acid residues with similar chemical properties (e.g., charge, hydrophobicity, or steric effects), and therefore do not change the functional properties of the molecule.

Therefore, when sequences differ by conservative substitutions, the percent sequence identity may be adjusted upwards to correct for the conservative nature of the substitution at the site of the non-identical residue. Sequences that differ by such conservative substitutions are said to have "sequence similarity" or "similarity." Techniques for making this adjustment are well known to those of ordinary skill in the art. Typically, such techniques involve scoring a conservative substitution as a partial, rather than a full, mismatch, thereby increasing the percentage sequence identity. For example, where an identical amino acid is given a score between 0 and 1, and a non-conservative substitution is given a score of 0, a conservative substitution is given a score between 0 and 1. The scoring of conservative substitutions may be calculated, for example, as implemented in the program PC/GENE (Intelligenetics, Mountain View, Calif.).

As used herein, the term "percentage of sequence identity" may refer to the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. Computer programs that may be used to determine identity and similarity between two sequences include: the GCG program package (Devereux et al. (1984) Nucleic Acids Res. 12(1):387); BLASTP; BLASTN; FASTA; and TFASTA (Atschul et al. (1990) J. Mol. Biol. 215:403).

Statistically associated: As used herein, the term "statistically associated" refers to the tendency of two events to occur together at a frequency greater than that attributable to chance, where the frequency attributable to chance is represented by a predetermined level of significance. Statistical association can be determined by any one of a number of significance tests well known to those in the art, for example, ANOVA or t-tests. See, e.g., *Statistical Methods*, G. W. Snedecor and W. G. Cochran, Iowa State University Press, Ames, Iowa (1985). Significance levels for alpha are preferably less than 0.01. For example, levels of significance for this invention could range between 0 and about 0.250, e.g., less than about 0.0001, 0.00050, 0.0010, 0.0050, 0.010, 0.025, 0.050, 0.100, or 0.250, including any levels therebetween.

Trait or phenotype: The terms "trait" and "phenotype" are used interchangeably herein. For the purposes of the present disclosure, traits of particular interest include, for example and without limitation: high oleic acid content; low linolenic acid content; imidazolinone resistance; clubroot disease resistance; and fertility restoration of cytoplasmic male sterility.

III. HO/LL Mutations in fad2 and fad3 Genes

Some embodiments include mutations in fad2 and fad3 genes that confer a HO/LL (High Oleic (fad2) and Low Linolenic (fad3)) phenotype in plants of the genus, *Brassica*. Some embodiments of the invention utilize an isolated nucleic acid molecule comprising nucleic acid sequences comprising one or both of these mutations to confer either or both of the HO/LL traits to a plant into which the isolated nucleic acid molecule is introduced. Such isolated nucleic acid molecules may additionally comprise a marker that is tightly linked to the HO and/or LL phenotype in canola.

*B. napus* varieties DMS100 (mutant type) and Quantum (wild-type) were used in the cloning of fad2 (fatty acid desaturase-2) and fad3 (fatty acid desaturase-3) alleles. The mutant DMS100 variety was derived from an $F_4$ bulk of a single $F_3$ plant selection originating from the cross of Global X AG019 sister line. DMS100 is a HO/LL line with an oleic acid content of about 77% and a linolenic acid content of about 3%. Quantum is a commercial wild-type variety that contains a comparatively low oleic acid (~66%) content, and high linolenic acid (~7%) content. As discussed in detail herein, sequencing of DMS100 genomic clones of fad2 and fad3 desaturase enzymes involved in the fatty acid synthesis pathway revealed single nucleotide mutations in each of the genes. Further sequence analyses show the mutations to be the cause of altered fatty acid contents in DMS100. These two mutations are distinct from previously published mutations (Tanhuanpää et al. (1998) Mol. Breeding 4:543-50; Jourdren et al. (1996) Theor. Appl. Genet. 93:512-8).

Some embodiments take advantage of the identification of a single nucleotide polymorphism (SNP) in the fad2 gene that is associated with particular oil contents that may be desirable in some applications. Oleic acid (C18:1) content in canola is influenced by a fad2 gene that encodes an enzyme (endoplasmic delta 12 oleate desaturase) responsible for the desaturation of oleic acid to linoleic acid (C18:2). Particular embodiments include a single nucleotide substitution mutation that introduces a premature "STOP" codon in the fad2 open reading frame, resulting in a truncated expression product. In certain embodiments, the single nucleotide substitution mutation is located at position 411 of the fad2 gene (see FIG. 1). For example, the mutation may be a "C" to "T" mutation at position 411 that creates the stop codon, "TAG," and results in a fad2 expression product that is only 185 amino acids in length. In some embodiments, a single nucleotide substitution mutation in the fad2 gene results in a truncated expressed polypeptide that has reduced function (e.g., no function or essentially no function) as an active desaturase for the desaturation of oleic acid to linoleic acid.

An inactivating mutant allele of the fad2 gene contributes to the control of oleic acid content in canola by reducing the desaturation of oleic acid to linoleic acid. In embodiments, the fad2 mutant allele comprises a nucleotide sequence that is specifically hybridizable to the complement of SEQ ID NO:7 in a region comprising the nucleotide at position 411, as determined by alignment with SEQ ID NO:7. In particular embodiments, the fad2 mutant allele is SEQ ID NO:7. In some embodiments, the invention also includes those nucleotide sequences which are substantially identical to the mutant fad2 allele of SEQ ID NO:7. For example, in some embodiments, a nucleic acid molecule is a fad2 homologue (e.g., an ortholog) that is at least about 85% identical to the mutant fad2 allele of SEQ ID NO: 7. A fad2 homologue may be 86%; 87%; 88%; 89%; 90%; 91%; 92%; 93%; 94%; 95%; 96%; 97%; 98%; 99%; 99.5%; or 99.8% identical to the mutant fad2 allele of SEQ ID NO:7. Such a fad2 homologue may be readily identified and isolated from any complete or partial genomes readily available to those of skill in the art for a variety of organisms, for example, a *Brassica* spp.

Some embodiments also include functional variants of the mutant fad2 allele of SEQ ID NO:7. Functional variants of fad2 include, for example, the fad2 sequence of SEQ ID NO:7, the sequence comprising one or more nucleotide substitutions, deletions, or insertions, wherein the functional variant reduces the desaturation of oleic acid to linoleic acid in a *Brassica* cell, as may be measured by routine techniques well-known to those of ordinary skill in the art. For example, the capability of a particular variant of the fad2 gene to reduce the desaturation of oleic acid to linoleic acid in a *Brassica* cell may be determined by homologous recombination of the mutation or fragment into a plant homozygous for a functional Fad2 allele, followed by routine isolation and characterization of seed oils from the plant. Functional variants of the fad2 gene may be created by site-directed mutagenesis, induced mutation, or they may occur as allelic variants (polymorphisms, e.g., SNPs). Particular embodiments include a mutation that introduces a premature "STOP" codon in the fad2 open reading frame, resulting in a truncated and inactive expression product.

Some embodiments take advantage of the identification of a single nucleotide polymorphism (SNP) in the fad32 gene that is associated with particular oil contents that may be desirable in some applications. The fad3 gene encodes for endoplasmic delta-15 linoleic desaturase, an enzyme responsible for the desaturation of linoleic acid (C18:2) to linolenic acid (C18:3). The fad32 gene in particular contributes to the control of linolenic acid content. Particular embodiments include a single nucleotide substitution mutation that interferes with correct splicing of the fad32 gene and thereby produces an incompletely translated expression product. In certain embodiments, the single nucleotide substitution mutation is located at the first base of a 5' splice site of an intron in the fad32 gene. The intron may be, for example, the third intron in the fad32 gene of *B. napus*, the sixth intron in the fad32 gene of *B. rapa*, or a homologous intron in the fad32 gene of a further plant species. For example, the mutation may be a "G" to "A" mutation at the first base of a 5' splice site of the third intron in the *B. napus* fad32 gene that interferes with correct splicing of the gene (see FIG. 3). In some embodiments, a single nucleotide substitution mutation that interferes with correct splicing of the fad32 gene and thereby produces an incompletely translated expression product may lead to an inactive enzyme and block the desaturation of linoleic acid (C18:2) to linolenic acid (C18:3), ultimately resulting in a decrease of C18:3 accumulation in canola seeds.

An inactivating mutant allele of a fad3 gene contributes to the control of linolenic acid content in canola, by reducing the desaturation of linoleic acid to linolenic acid. In embodiments, the fad3 mutant allele comprises a nucleotide sequence that is specifically hybridizable to the complement of SEQ ID NO:12 in a region comprising the nucleotide at the first base of a 5' splice site of an intron in the fad32 gene, as determined by alignment with SEQ ID NO:12. In particular embodiments, the fad3 mutant allele is SEQ ID NO:12. In some embodiments, the invention also includes those nucleotide sequences which are substantially identical to the mutant fad3 allele of SEQ ID NO:12. For example, in some embodiments, a nucleic acid molecule is a fad3 homologue (e.g., an ortholog) that is at least about 85% identical to the mutant fad3 allele of SEQ ID NO:12. A fad3 homologue may be 86%; 87%; 88%; 89%; 90%; 91%; 92%; 93%; 94%; 95%; 96%; 97%; 98%; 99%; 99.5%; or 99.8% identical to the mutant fad3 allele of SEQ ID NO:12. Such a fad3 homologue may be readily identified and isolated from any complete or partial genomes readily available to those of skill in the art for a variety of organisms, for example, a *Brassica* spp.

Some embodiments also include functional variants of the mutant fad3 allele of SEQ ID NO:12. Functional variants of fad3 include, for example, the fad3 sequence of SEQ ID NO:12, the sequence comprising one or more nucleotide substitutions, deletions, or insertions, wherein the functional variant reduces the desaturation of linoleic acid to linolenic acid in a *Brassica* cell, as may be measured by routine techniques well-known to those of ordinary skill in the art. For example, the capability of a particular variant of the fad3 gene to reduce the desaturation of linoleic acid to linolenic acid in a *Brassica* cell may be determined by homologous recombination of the mutation or fragment into a plant homozygous for a functional Fad3 allele, followed by routine isolation and characterization of seed oils from the plant. Functional variants of the fad3 gene may be created by site-directed mutagenesis, induced mutation, or they may occur as allelic variants (polymorphisms, e.g., SNPs). Particular embodiments include a mutation that introduces a premature "stop" codon in the fad2 open reading frame, resulting in an incompletely translated expression product.

IV. Molecular Markers and their Use

Embodiments of the present invention include molecular markers (i.e., nucleic acid markers) that are linked (e.g., linked; tightly linked; or extremely tightly linked) to a gene of interest (e.g., fad2 or fad3). For example, a gene of interest in some embodiments may be a gene contributing to a phenotype or trait in *Brassica* selected from the group consisting of high oleic acid, low linolenic acid, herbicide resistance (e.g., glyphosate resistance and imidazolinone resistance), and clubroot disease resistance. Particular embodiments include a method for using such markers, for example, to transfer the gene of interest (e.g., as comprised in a segment of DNA), to introduce the gene of interest into a host, and to identify the gene of interest in an organism or DNA sample from an organism. In particular embodiments, a SSR marker may be used to transfer a segment of DNA comprising a gene contributing to clubroot disease resistance from a clubroot disease-resistant *B. napus* variety. Such an SSR marker may include a contiguous segment of genomic DNA that is 300 bp in length and is amplified by the exemplary primers of SEQ ID NOs:18 and 19.

In some embodiments, markers flanking a gene of interest may be used to transfer segment(s) of donor parent DNA that unequivocally contain the gene of interest. In particular embodiments, markers in *B. napus* linkage group N5 and N1, or markers equivalent to such markers, may be used to transfer a segment of DNA comprising fad2 from *B. napus* variety, DMS100. In these and further embodiments, markers in *B. napus* linkage group N14 and N4, or markers equivalent to such markers, may be used to transfer a segment of DNA comprising fad32 from *B. napus* variety, DMS100.

In some embodiments, a method for using markers flanking a gene of interest to transfer segment(s) of donor parent DNA that unequivocally contain the gene of interest may comprise analyzing the genomic DNA of two parent plants with probes that are specifically hybridizable to markers linked to the gene of interest; sexually crossing the two parental plant genotypes to obtain a progeny population, and analyzing those progeny for the presence of the markers linked to the gene of interest; backcrossing the progeny that contain the markers linked to the gene of interest to the recipient genotype to produce a first backcross population, and then continuing with a backcrossing program until a final progeny is obtained that comprises any desired trait(s) exhibited by the parent genotype and the gene of interest. In particular embodiments, individual progeny obtained in each crossing and backcrossing step are selected by marker analysis at each generation. In some embodiments, analysis of the genomic DNA of the two parent plants with probes that are specifically hybridizable to markers linked to the gene of interest reveals that one of the parent plants comprises fewer of the linked markers to which the probes specifically hybridize, or none of the linked markers to which the probes specifically hybridize.

In some embodiments, a marker that is linked to a gene of interest may be used to introduce the gene of interest into a plant of the genus, *Brassica*, by genetic transformation. In particular embodiments, a marker in *B. napus* linkage group N5 or N1, or a marker equivalent to such a marker, may be used to transfer a fad2 gene into a plant of the genus, *Brassica*. In these and further embodiments, a marker in *B. napus* linkage group N14 or N4, or a marker equivalent to such a marker, may be used to transfer a fad32 gene into a plant of the genus, *Brassica*. In these and further embodiments, a SSR marker may be used to transfer a gene contributing to clubroot disease resistance into a plant of the genus, *Brassica*. Such an SSR marker may include a contiguous segment of genomic DNA that is 300 bp in length and is amplified by the exemplary primers of SEQ ID NOs:18 and 19.

In some embodiments, a method for introducing a gene of interest into a plant of the genus, *Brassica*, by genetic recombination may comprise analyzing the genomic DNA of a plant (e.g., *B. napus* variety, DMS100) with a probe that is specifically hybridizable to a marker linked to the gene of interest to identify the gene of interest in the plant; isolating a segment of the genomic DNA of the plant comprising the gene of interest, for example, by extracting the genomic DNA and digesting the genomic DNA with one or more restriction endonuclease enzymes; optionally amplifying the isolated segment of DNA; introducing the isolated segment of DNA into a cell or tissue of a host plant of the genus, *Brassica*; and analyzing the DNA of the host plant with a probe that is specifically hybridizable to a marker linked to the gene of interest to identify the gene of interest in the host plant. In particular embodiments, the isolated segment of DNA may be introduced into the host plant such that it is stably integrated into the genome of the host plant.

In some embodiments, a marker that is linked to a gene of interest may be used to introduce the gene of interest into an organism (e.g., a plant) other than a plant of the genus, *Brassica*. In particular embodiments, the gene of interest is fad2, and the marker is in *B. napus* linkage group N5 or N1, or is an equivalent marker. In particular embodiments, the gene of interest is fad3, and the marker is in *B. napus* linkage group N14 or N4, or is an equivalent marker. In particular embodiments, the gene of interest is a gene contributing to clubroot disease resistance, and the marker is a SSR marker including a contiguous segment of genomic DNA that is 300 bp in length that is amplified by the exemplary primers of SEQ ID NOs:18 and 19, or an equivalent marker.

In some embodiments, a method for introducing the gene of interest into an organism (e.g., a plant) other than a plant of the genus, *Brassica*, may comprise analyzing the genomic DNA of a *Brassica* plant (e.g., a plant of *B. napus* variety DMS100) with a probe that is specifically hybridizable to a marker linked to the gene of interest to identify the gene of interest in the plant; isolating a segment of the genomic DNA of the plant comprising the gene of interest, for example, by extracting the genomic DNA and digesting the genomic DNA with one or more restriction endonuclease enzymes; optionally amplifying the isolated segment of DNA; introducing the isolated segment of DNA into an organism other than a plant of the genus, *Brassica*; and analyzing the DNA of the organism with a probe that is specifically hybridizable to a marker linked to the gene of interest to identify the gene of interest in the organism. In particular embodiments, the isolated segment of DNA may be introduced into the organism such that it is stably integrated into the genome of the organism.

In some embodiments, markers that are linked to a gene of interest may be used to identify a plant comprising the gene of interest. In particular embodiments, the plant may be a *Brassica* spp. In some embodiments, nucleic acid molecules (e.g., genomic DNA or mRNA) may be extracted from the plant. The extracted nucleic acid molecules may then be contacted with a probe that is specifically hybridizable to a marker linked to the gene of interest. Specific hybridization of the probe to the extracted nucleic acid molecules is indicative of the presence of the gene of interest in the plant.

General information regarding molecular markers and methods of their use may be found, for example, in Andrew H. Paterson, "The DNA Revolution" (Chapter 2) in: *Genome Mapping in Plants*. Ed. Andrew H. Paterson, 1996, Academic Press/R. G. Landis Company, Austin, Tex., pp. 7-21.

V. Molecular Markers for fad2 and fad3 Genes

Molecular markers that are linked (e.g., tightly-linked) to each of the mutant alleles, fad2 and fad3, in *Brasicca* spp. are provided. DNA segments containing sequences involved in the HO trait (fad2) and LL trait (fad3) are identified. These segments are located around and between markers that are linked (e.g., tightly-linked) to the mutant alleles in a genomic linkage group. Thus, nucleic acid molecules comprising a mutant fad2 or fad3 gene having an inactivating mutation are also provided. The segments identified, and the markers thereof, are described herein, in part, by their position in linkage groups in the *B. napus* genome. For example, fad2 and molecular markers linked thereto may be located in linkage groups N5 and N1. Also in examples, fad3 and molecular markers linked thereto may be located in linkage groups N14 and N4.

The position of the segments identified, and the markers thereof, may be expressed as recombination frequencies or map units. The embodiments described herein were performed in *B. napus* population, DMS100× Quantum. However, the positions of particular segments and markers as map units may be expressed with reference to a *Brassica* inbred genome sequence. It is expected that numbers given for particular segments and markers as map units may vary from cultivar to cultivar, and are not part of the essential definition of the DNA segments and markers, which DNA segments and markers are otherwise described, for example, by nucleotide sequence.

Specific exemplary inactivating single nucleotide mutations in the fad2 and fad32 genes present in germplasm of the canola line, DMS100, are factors that account for increased oleic acid (HO) and decreased linolenic acid (LL) contents that are observed in this line. Using molecular markers linked to either or both of these mutations, marker-assisted introgression may be used to introduce into canola lines the HO/LL traits of DMS100 and its progeny or derivatives, and/or the mutated fad2 and fad32 genes of DMS100 and its progeny or derivatives (SEQ ID NO:7 (see FIG. 1) and SEQ ID NO:12 (see FIG. 3), respectively).

Methods of using nucleic acid molecular markers that are linked to or that reside within a mutant fad2 or fad3 allele to introduce HO/LL traits into new plants and germplasms, as well as to identify plants with HO/LL traits, may result in a cost savings for plant developers, because such methods may reduce or eliminate the need to phenotype the progenies of crosses intended to introduce HO/LL traits.

In embodiments, a marker that is extremely tightly linked to the HO trait is a "T" nucleotide at position 411 of the *B*.

napus fad2 gene (or the same position of an aligned sequence from, e.g., a *Brassica* spp.), as described in FIG. 1 and represented in SEQ ID NO:7. In embodiments, a marker that is extremely tightly linked to the LL trait is an "A" nucleotide at the first base of a 5' splice site of the third intron in the *B. napus* fad32 gene (or the same position of an aligned sequence from, e.g., a *Brassica* spp.), as described in FIG. 3 and represented in SEQ ID NO:12. Additional markers can be identified as equivalent to either of these exemplary markers, for example, by determining the frequency of recombination between the additional marker and the exemplary marker. Such determinations my utilize an improved method of orthogonal contrasts based on the method of Mather (1931), *The Measurement of Linkage in Heredity*, Methuen & Co., London, followed by a test of maximum likelihood to determine a recombination frequency. Allard (1956) Hilgardia 24:235-78. If the value of the recombination frequency is less than or equal to 0.10 (i.e., 10%) in any cultivar, then the additional marker is considered equivalent to the particular reference marker for the purposes of use in the presently disclosed methods.

Markers that are extremely tightly linked to the high oleic acid (HO) trait include means for introducing a HO phenotype into a plant of the genus, *Brassica*. Means for introducing a HO phenotype into a plant of the genus, *Brassica*, may include a nucleic acid sequence from a plant, the detection of which nucleic acid provides at least a strong indication that the plant comprises a nucleic acid sequence comprising a mutant fad2 allele that contributes to the HO trait. An example of a means for introducing a HO phenotype into a plant of the genus, *Brassica*, is a "T" nucleotide at position 411 of the *B. napus* fad2 gene, as described in FIG. 1 and represented in SEQ ID NO:7. Markers that are extremely tightly linked to the low linolenic acid (LL) trait include a means for introducing a LL phenotype into a plant of the genus, *Brassica*. Means for introducing a LL phenotype into a plant of the genus, *Brassica*, may include a nucleic acid sequence from a plant, the detection of which nucleic acid provides at least a strong indication that the plant comprises a nucleic acid sequence comprising a mutant fad32 allele that contributes to the LL trait. An example of a means for introducing a LL phenotype into a plant of the genus, *Brassica*, is an "A" nucleotide at the first base of a 5' splice site of the third intron in the *B. napus* fad32 gene, as described in FIG. 3 and represented in SEQ ID NO:12.

Related to markers that are extremely tightly linked to the high oleic acid (HO) trait are means for identifying a plant carrying a gene contributing to a HO phenotype in a plant of the genus, *Brassica*. Such means include a molecule that presents a detectable signal when added to a sample obtained from a plant carrying a gene contributing to a HO phenotype in a plant of the genus, *Brassica*. Specific hybridization of nucleic acids is a detectable signal, and a nucleic acid probe that specifically hybridizes to a gene contributing to a HO phenotype may therefore be a means for identifying a plant carrying a gene contributing to a HO phenotype in a plant of the genus, *Brassica*. In some examples, a means for identifying a plant carrying a gene contributing to a HO phenotype in a plant of the genus, *Brassica*, is a probe that specifically hybridizes to a segment of the *B. napus* fad2 gene comprising a "C" to "T" mutation at position 411, but does not hybridize to the same segment of the wild-type *B. napus* fad2 gene (e.g., SEQ ID NO:5).

Related to markers that are extremely tightly linked to the low linolenic acid (LL) trait are means for identifying a plant carrying a gene contributing to a LL phenotype in a plant of the genus, *Brassica*. Such means include a molecule that presents a detectable signal when added to a sample obtained from a plant carrying a gene contributing to a LL phenotype in a plant of the genus, *Brassica*. Specific hybridization of nucleic acids is a detectable signal, and a nucleic acid probe that specifically hybridizes to a gene contributing to a LL phenotype may therefore be a means for identifying a plant carrying a gene contributing to a LL phenotype in a plant of the genus, *Brassica*. In some examples, a means for identifying a plant carrying a gene contributing to a LL phenotype in a plant of the genus, *Brassica*, is a probe that specifically hybridizes to a segment of the *B. napus* fad32 gene comprising a "G" to "A" mutation at the first base of a 5' splice site of the third intron, but does not hybridize to the same segment of the wild-type *B. napus* fad32 gene (e.g., SEQ ID NO:15).

VI. Markers for Clubroot Disease Resistance

Molecular markers that are linked (e.g., tightly-linked) to clubroot disease resistance in *Brassica* are provided. DNA segments containing gene(s) involved in clubroot disease resistance are linked to these markers. Thus, nucleic acid molecules comprising a gene that is involved in clubroot disease resistance are able to be utilized and manipulated using the provided markers. The markers identified, and the sequences linked thereto, may be described, in part, by their position in linkage groups in a *B. napus* genome. In some examples, a marker that is linked to clubroot disease resistance in *Brassica* is a SSR marker.

The embodiments described herein were performed in a *B. napus* population obtained by crossing the clubroot disease-resistant variety, Mendel, with a HO/LL *B. napus* inbred containing a fertility restoration gene (restr) and glyphosate resistance (gly). The position of the markers identified, and the DNA sequences (e.g., genes) linked thereto, may be expressed as recombination frequencies or map units. The positions of particular sequences and markers as map units may be expressed with reference to a *Brassica* inbred genome sequence. It is expected that numbers given for particular sequences and markers as map units may vary from cultivar to cultivar, and are not part of the essential definition of any DNA sequences or markers, which DNA sequences and markers may be otherwise described, for example, by nucleotide sequence.

Markers present in germplasm of the canola line, Mendel, may be linked to factor(s) that account for the clubroot disease resistance that is observed in this clubroot disease resistance source line. For example, by using these markers or their equivalents, marker-assisted introgression may be used to introduce into canola lines the clubroot disease resistance of Mendel and its progeny or derivatives.

A marker that is linked to clubroot disease resistance in *Brassica* can be integrated into a marker-assisted selection program for the development of new clubroot disease-resistant genotypes and germplasm. Such a program allows the screening of thousands of *Brassica* progeny derived, for example, from crossing *Brassica* inbreds having one or more desirable traits and Mendel (or its progeny or derivatives). Such a marker also allows the comparatively rapid and inexpensive identification of clubroot disease-resistant lines, before utilization of resources such as greenhouses, fields, etc. during biological screening in a clubroot disease infection assay. Currently, disease resistance screening is typically carried out in restricted indoor greenhouse trails, which are conducted at considerable expense.

In embodiments, a marker that is linked to the clubroot disease resistance phenotype is a SSR marker comprising a contiguous segment of genomic *B. napus* DNA that is 300 bp in length and is amplified by the exemplary primers of SEQ ID NOs:18 and 19, which marker is linked to clubroot disease resistance in a *B. napus* plant. It will be recognized by those of skill in the art that equivalent markers at the same locus may be defined by altering the length or position of the primers used to change the length of the contiguous segment of genomic *B. napus* DNA that is amplified by the primers.

Additional markers can be identified as equivalent to this exemplary marker, for example, by determining the frequency of recombination between the additional marker and the exemplary SSR marker. Such determinations may utilize an improved method of orthogonal contrasts based on the method of Mather (1931), *The Measurement of Linkage in Heredity*, Methuen & Co., London, followed by a test of maximum likelihood to determine a recombination frequency. Allard (1956) Hilgardia 24:235-78. If the value of the recombination frequency is less than or equal to 0.10 (i.e., 10%) in any cultivar, then the additional marker is considered equivalent to the particular reference marker for the purposes of use in the presently disclosed methods.

Markers that are linked to clubroot disease resistance include means for introducing clubroot disease resistance into a plant of the genus, *Brassica*. Means for introducing clubroot disease resistance into a plant of the genus, *Brassica*, may include a nucleic acid sequence from a plant, the detection of which nucleic acid provides at least a strong indication that the plant comprises a nucleic acid sequence comprising a DNA sequence that contributes to the clubroot disease resistance phenotype. An example of a means for introducing clubroot disease resistance into a plant of the genus, *Brassica*, is a contiguous segment of genomic DNA that is 300 bp in length and is amplified by the exemplary primers of SEQ ID NOs:18 and 19, which marker is linked to clubroot disease resistance in a *B. napus* plant.

Related to markers that are linked to clubroot disease resistance are means for identifying a plant carrying a gene contributing to clubroot disease resistance in a plant of the genus, *Brassica*. Such means include a molecule that presents a detectable signal when added to a sample obtained from a plant carrying a gene contributing to clubroot disease resistance in a plant of the genus, *Brassica*. Specific hybridization of nucleic acids is a detectable signal, and a nucleic acid probe that specifically hybridizes to a DNA sequence contributing to a clubroot disease resistance phenotype may therefore be a means for identifying a plant carrying a gene contributing to clubroot disease resistance in a plant of the genus, *Brassica*. In some examples, a means for identifying a plant carrying a gene contributing to clubroot disease resistance in a plant of the genus, *Brassica*, is a probe that specifically hybridizes to a contiguous segment of genomic DNA that is 300 bp in length and is amplified by the exemplary primers of SEQ ID NOs:18 and 19, but does not hybridize to any segment amplified by the same primers from wild-type genomic DNA.

In addition to the foregoing, the primers set forth as SEQ ID NOs:18-22, or their equivalents, may be used in embodiments to screen for the presence of a gene involved in clubroot disease resistance. When these primers, or their equivalents, are used to amplify intervening DNA sequences from a genomic *Brassica* DNA sample, the amplified DNA fragments may be visualized (e.g., by gel electrophoresis). The presence of a 300 bp fragment (or a fragment of a size expected for the use of primers functionally equivalent to SEQ ID NOs:18-22), indicates that the plant from which the genomic DNA sample was obtained comprised a gene involved in clubroot disease resistance.

VII. Herbicide and Clubroot Disease Resistant HO/LL *Brassica* Plants

Some embodiments of the invention provide or otherwise include a *Brassica* plant (e.g., a *B. napus* plant) that has high oleic acid and/or low linolenic acid (HO/LL) when compared to a wild-type *Brassica* plant of the same species (e.g., *B. napus* variety Quantum). In these and further embodiments, a *Brassica* plant may comprise the trait of resistance to an imidazolinone herbicide. In these and further embodiments, a *Brassica* plant may comprise the trait of resistance to clubroot disease. Thus, some embodiments of the invention provide or otherwise include a *Brassica* plant comprising all the traits of high oleic acid, low linolenic acid, imidazolinone resistance, and clubroot disease resistance.

Thus, a *Brassica* plant that is resistant to clubroot disease may comprise a marker linked to the clubroot disease resistance phenotype, and also comprise a marker linked to the HO trait. In these and other embodiments, a *Brassica* plant may also comprise a genetic marker linked to the LL trait. For example, a *Brassica* plant resistant to clubroot may also comprise one or more nucleic acid sequences corresponding to mutated fad2 and/or fad3 genes. These genes may be introduced into canola or other oil seed plants by any of a number of known methods in the art. Additionally, wild-type fad2 and/or fad3 genes may be altered by known in vivo or in vitro methods to provide exemplary mutated fad2 and/or fad3 genes, or their equivalents. Examples of such genes, markers, and mutations may be found in, but are not limited to, those disclosed U.S. Patent Publication No. 2006/0248611 (the entirety of the contents of which are incorporated herein by this reference).

In particular embodiments, a seed of a *Brassica* plant may comprise a favorable oil profile. For example, the seed may comprise at least 63%, 64%, 65%, 66%, 67%, 68%, 69%, 70%, 71%, 72%, 73%, 74%, 75%, 76%, or 77% oleic acid (C18:1). In these and other examples, the seed of a *Brassica* plant may comprise not more than 6%, 5%, 4%, 3%, 2%, or 1.5% linoleic acid (C18:3).

In embodiments of the invention, the *B. napus* plants resistant to clubroot may also be resistant or tolerant to an imidazolinone.

In some embodiments, a clubroot disease resistant *Brassica* plant may also comprise a cytoplasmic male sterility system restorer. Cytoplasmic male sterility (CMS) is a widespread and classic non-Mendelian trait. CMS plants are incapable of self-pollination. Therefore, when a CMS line is planted alongside a male-fertile line, all the seed that forms on the sterile plants will be a hybrid of the two parents. Unlike most traits, CMS is maternally transmitted (i.e., it is passed to offspring only through the seed parent). This property results from the fact that the gene or genes that determine CMS are located on mitochondrial DNA (mtDNA). Unlike most genes, which reside in nuclear DNA, genes in mtDNA are transmitted solely through the female in most plant species. As a result of this property of maternal transmission, it is possible to easily propagate female CMS lines by pollinating with a male fertile "maintainer" line, that is identical to the CMS line in its nuclear genes, but which is male fertile due to the absence of CMS-causing mtDNA. However, as a result of the maternal transmission of CMS, hybrid plants produced using female CMS lines are also male sterile; they carry the male sterility-conferring mtDNA. This is problematic for seed crops (e.g., maize and canola) that require pollen production for the formation of the harvested product seed.

Figure 6:
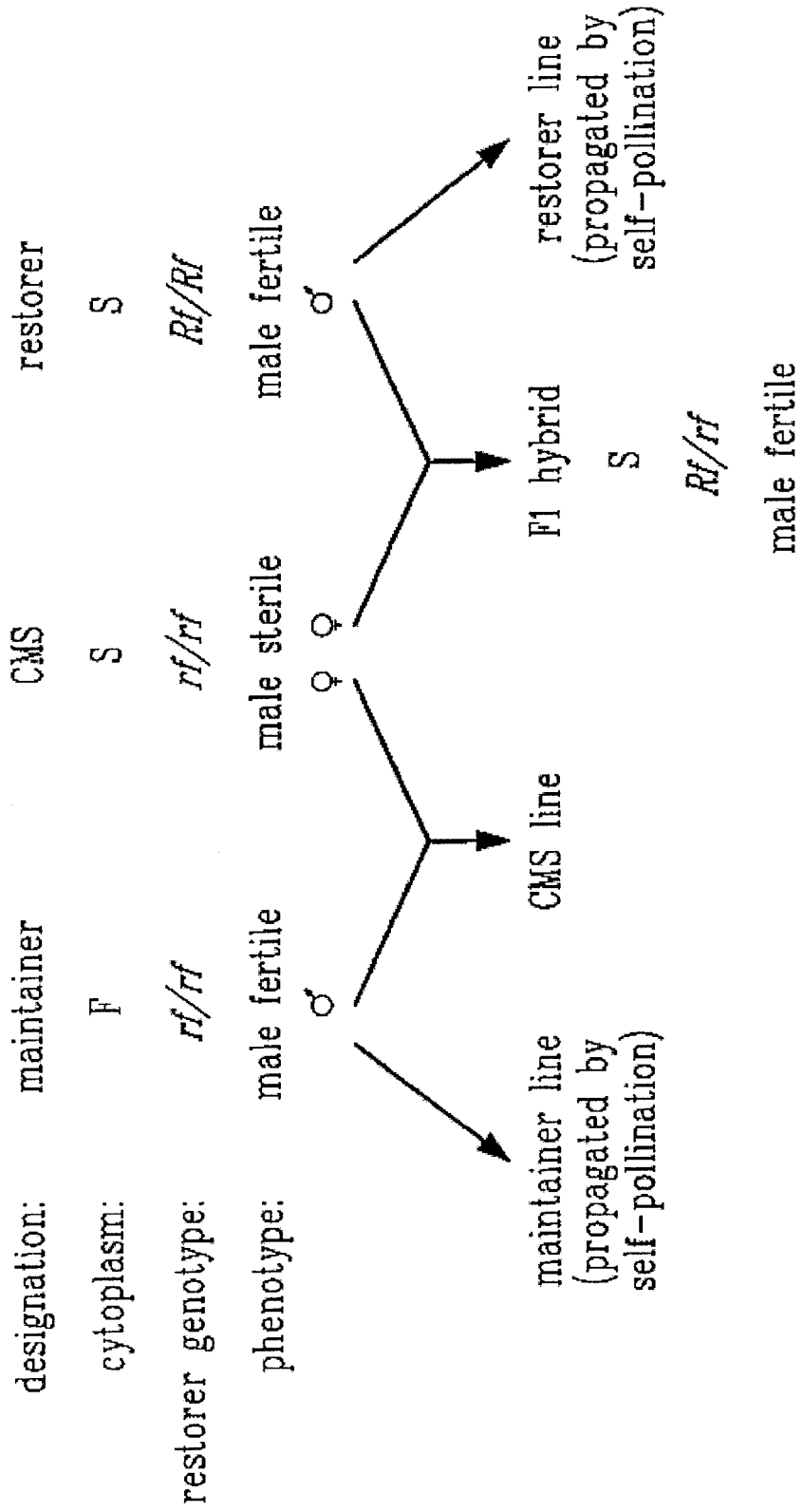
FIG. 6 includes a schematic representation of one use of a cytoplasmic male sterility system in a hybrid seed production scheme.

Fortunately, in many crop species, specific dominant nuclear genes termed restorers of fertility (Rf) have been identified that can suppress the male sterile phenotype, and "restore" fertility to F hybrids. Thus, the components of a CMS system comprise: (1) the CMS line (which contains the male sterile (S) cytoplasm (or mtDNA), and is homozygous for the recessive or maintainer allele of the restorer gene); (2) the maintainer line (which contains a fertile or normal mtDNA (F), but is isogenic with the CMS line at nuclear genetic loci), and (3) the restorer line (which usually contains the male sterile mtDNA, but is homozygous for the dominant nuclear Rf gene). The use of these components in a hybrid seed production scheme is illustrated in FIG. 6. Male sterility systems and restorers useful in the present invention include, but are not limited to: the polima system; the Ogura system; the system described in U.S. Pat. No. 6,365,798; and the system described in U.S. Patent Publication No. 2004/0237141 (the entirety of the contents of each of which are incorporated herein by this reference).

All publications, patents, and patent applications cited herein are hereby incorporated by reference. Unless otherwise noted herein, standard methods of DNA purification, restriction enzyme digestion, agarose gel analysis, DNA fragment isolation, ligation and transformation may be used for purposes of the present invention. Such methods are described in, for example, Sambrook et al. (1989) *Molecular Cloning: A Laboratory Manual, 2nd Ed.*, Cold Spring Harbor Laboratory Press; and Ausubel et al. (1987) *Current Protocols in Molecular Biology*, John Wiley and Sons, New York (both of which are incorporated by reference herein).

The following examples are provided to illustrate certain particular features and/or embodiments. The examples should not be construed to limit the disclosure to the particular features or embodiments exemplified. It is to be expected that those skilled in the art may discern and practice variations of or alternatives to the specific teachings provided herein, without departing from the scope of the present invention.

EXAMPLES

Example 1

Materials and Methods

Plant Material

Canola varieties DMS100 (mutant type) and Quantum (wild type) were used in this study for cloning of fad2 (fatty acid desaturase-2) and fad3 (fatty acid desaturase-3) alleles. DMS100 is a HO/LL (High Oleic and Low Linolenic) line with oleic acid content at about 77% and linolenic acid content at about 3%. DMS100 is derived from an $F_4$ bulk of a single $F_3$ plant selection originating from the cross of Global× AG019 sister line. Quantum is a commercial variety and contains low oleic acid (~66%) and high linolenic acid (~7%) content. A doubled haploid (DH) population was developed by microspore culture from $F_1$ plants of the cross between canola line Quantum and DMS100. The DH population comprised of 604 lines. A complete fatty acid analysis of the seeds of the DH lines and their parents was implemented by using gas chromatography. Of the 604 DH lines, 183 were randomly selected for marker analysis and mapping.

Genomic DNA Extraction and Quantification

DNA of both parental lines and 183 DH lines was extracted from the leaves of two-week-old greenhouse-grown plants using Qiagen DNeasy™ 96 Plant Test Kit. The details of DNA extraction procedures are described in the DNeasy™ 96 Plant Test Kit Handbook. This kit allowed DNA to be extracted in a 96-well format for a high throughput extraction.

For DNA quantification, PicoGreen™ dye was diluted 200-fold into 1×TE buffer. In a microtiter plate, 100 μl of the diluted PicoGreen™ dye solution were added into each well and then 5 μl of each DNA sample or DNA standards (5 μg/ml, 10 μg/ml and 20 μg/ml) were added. The plate was then agitated on a plate shaker briefly and read using the Spectra Max GEMINIS™ XS microplate fluorometer from Molecular Devices.

PCR Amplification

PCR amplification reactions contained 20 to 30 ng of genomic DNA, 0.25 μM 10-mer primer, 2.5 mM $MgCl_2$, 0.2 mM of each dNTP, 1×PCR buffer and 0.6 units of Taq DNA polymerase. Amplifications were performed in a GeneAmp PCR System 9700 programmed for 35 cycles of 45 seconds at 94° C., 30 seconds at 55° C. to 60° C., 1 minute at 72° C. and ending with 7 minutes at 72° C.

PCR amplification products of interest were resolved by agarose-gel electrophoresis, and the bands of interest were excised from the gel. The excised bands were placed in a microfuge tube containing sterilized water and heated for five minutes in boiling water. The dissolved DNA was amplified by PCR with the corresponding primer pairs. The amplified products were ligated to PCR2.1-TOPO cloning vector using a TA-cloning kit (Invitrogen Corp., San Diego, Calif.) according to the manufacturer's instructions. The ligated products were then transformed into competent cells and plated on LB-agar plates containing ampicillin or kanamycin, X-GAL and IPTG to enable white/blue selection. White colonies in the transformation plates were picked, and identifications of the cloned PCR products were verified by digestion with the restriction enzyme, EcoRI, which revealed the vector DNA fragment and the insert fragment of the expected size. The positive clones containing the insert were sequenced by Sequetech Corporation (Mountain View, Calif.).

Sequence and Data Analyses

The sequences were analyzed and aligned by using SeqWeb™ (version 2) web-based sequence analysis software in GCG software package (Wisconsin University). Linkage associations between the markers and high oleic or low linolenic (HO/LL) traits were determined by t-test analysis. The genetic linkage map was generated with JoinMap™ V2.0 computer software using a minimum LOD of 3.0. Map distance was converted to centiMorgans using the Kosambi function. Putative QTL regions associated with the C18:1 and C18:3 were located by interval mapping using the MapQTL V 3.0 software. The LOD score of 3.0 was used to identify regions potentially affecting the HO and LL traits.

Invader Assay

Invader Assay kits specific to fad2 and fad3 gene mutations were developed through Third Wave Technologies (Madison, Wis.). The concentration of DNA samples for the Invader Assay was normalized to 15 ng/μl using QiaGen Bio-Robot 3000 (Valencia, Calif.). Invader Assays were performed in 96-well plates per manufacturer's instruction. In brief, DNA samples were denatured at 95° C. for ten minutes. Seven μl of the denatured DNA (15 ng/μl) and 8 μl of reaction mix (3 μl oligo mix and 5 μl of 24 mM $MgCl_2$) were added into each well of 96-well Invader Assay plates. Then, each reaction was overlaid with 15 μl of mineral oil, and the plates were incubated in a BioOven III from St. John Associates, Inc. (Beltsville, Md.) at 63° C. for four hours. The reaction plates were read using the Spectra Max GEMINIS™ XS microplate fluorometer from Molecular Devices for fluorescent signals. Percent signal over background for the mutant allele was divided by the percent signal for wild-type allele for each sample to calculate the ratio. The genotypes of the samples were determined based on the calculated ratio.

Example 2

Cloning of fad2 and fad3 Alleles

Genomic DNA fragments from the fad2 gene of parental *B. napus* lines, DMS100 (mutant) and Quantum (wild-type), were amplified by using primers homologous to *Arabidopsis* or *B. rapa* fad2 gene sequences. Tanhuanpää et al. (1998), supra. FIG. 1. The fad2 fragments amplified from each of the parents by the primers FAD2-2F and FAD2-6R were cloned and sequenced. This primer pair amplified a fad2 fragment of the same length (986 bp) from each of the two parents. The sequences of these two primers are:

```
FAD2-2F:  CAATCCCTCGCTCTTTCTCCTACC (SEQ ID NO: 1)

FAD2-6R:  CCTTTCTTGTCACCTTCCCTGTCC (SEQ ID NO: 2)
```

Between the two parental lines, a single nucleotide substitution mutation was identified at position 411 of the fad2 gene. FIG. 1. The wild-type Quantum fad2 gene contains a "C" nucleotide at position 411. However, the HO/LL DMS100 fad2 gene contains a SNP at the same position, wherein the nucleotide is changed to a "T." The presence of a "T" at this position introduces a stop codon, and results in a severely truncated fad2 expression product that is only 185 amino acids in length. FIG. 2.

DNA sequences of the fad31 and fad32 loci for the endoplasmic delta-15 linoleic desaturase of *B. napus* were searched and retrieved from GenBank (accession numbers AF056569 (fad31) and AF066570 (fad32)). Three pairs of primers for each of the fad31 locus and the fad32 locus were designed from the fad31 and fad32 gene sequences using Primer Express primer designing software (PE Applied Biosystems, Foster City, Calif.). The fad31 fragments amplified by the primer pair BNFD31-CF (GAGGCTTGGACGAC-CACTTG) (SEQ ID NO:3) and BNFD31-CR (GACTGGAC-CAACGAGGAATG) (SEQ ID NO:4), and fad32 fragments amplified by the primer pair BNFD32-CF (CAA-GAATTTGTCCCACAGTACAC) (SEQ ID NO:16) and BNFD32-CR (CAACTGTTGTTAATCCTCCACG) (SEQ ID NO:17), from each of the parents were cloned. Seven DMS100 clones and six Quantum clones of fad31 and six DMS100 clones and six Quantum clones of fad32 were sequenced.

Sequence analysis and alignment revealed no sequence difference between DMS100 and Quantum clones for fad31 (data not shown). However, sequence alignment revealed a single nucleotide mutation ("G" to "A"), at the first base of 5' splice site of the third intron in the fad32 gene. FIG. 3. This intron corresponds to intron 6 of the fad3 gene in *B. rapa* (Tanhuanpää (2000) Mapping and cloning of Fad3 gene in *Brassica rapa* subsp. *Oleifera*. GenBank direct submission. GenBank Accession Nos. AF308975, AF308976, AF308977 and AF308978) and *Arabidopsis* (Nishiuchi et al. (1994) Plant Physiol. 105:767-8). The fad3 genes of *B. rapa* and *Arabidopsis* contain eight exons and seven introns, while the *B. napus* sequence examined herein covers exons 4 (partial), 5, 6, and 7 (partial) and introns 4, 5, and 6. This interpretation of exons/introns in the fad3 gene is supported by the fact that the fad3 gene sequence is highly conserved among sequenced *Brassica* species and *Arabidopsis*.

Plant introns contain highly conserved 5' splice sites (exon/intron junction—AG/GTAAG) and 3' splice sites (intron/exon junction—TGCAG/G). The first two nucleotides in the 5' splice site intron junction sequence, +1G and +2T, have shown 100% and 99% conservation, respectively, among over 1000 *Arabidopsis* introns studied. Lorković et al. (2000) Trends Plant Sci. 5(4):160-7; and Brown (1996) Plant Mol. Biol. 32(3):531-5. The accuracy of splicing depends on the mechanisms of intron signal recognition and the correct selection of 5' and 3' splice sites. The mutation of +1G to +1A at the 5' splice site (position 530) identified herein (see FIG. 3) may abolish splicing or lead to exon skipping; i.e., the affected exon (exon 6) and both flanking introns may be removed in a single splicing event. Lorković et al. (2000), supra; and Simpson et al. (1998) Plant J. 15(1):125-31. Such exon skipping may lead to synthesis of a polypeptide missing the amino acids encoded by the exon 6 of the fad3 gene. This mutation may also block splicing at the normal 5' splice site, and activate cryptic splice sites at different positions, which can cause cryptic splicing of the affected exon together with the downstream intron. McCullough et al. (1993) Mol. Cell. Biol. 13(3):1323-31. Such cryptic splicing may lead to early termination of translation and synthesis of a shorter polypeptide for delta-15 linoleate desaturase encoded by fad3, because the intron contains stop codons in all three possible reading frames and hence, exons 7 and 8 will remain untranslated. The incomplete translation of fad3 can inactivate the enzyme and block the desaturation of linoleic acid (C18:2) to linolenic acid (C18:3), resulting in the decrease of C18:3 accumulation in canola seeds.

These data strongly suggest that the single nucleotide mutations identified in the fad2 and fad3 genes are factors that account for the increase in oleic acid and decrease in linolenic acid contents in the canola line, DMS100. As shown in FIGS. 1 and 3, respectively, mutant-specific primers FAD2GM (CGCACCGTGATGTTAACGGTTT) (SEQ ID NO:5) and FAD3cGM (ATAAATAATGTTGATCTACTTAT) (SEQ ID NO:15) were designed for purposes of detecting the mutant HO/LL alleles of fad2 and fad32 using PCR amplification. Using molecular markers linked to either or both of the two mutations described, supra, marker-assisted introgression may be used to introduce into canola lines the HO/LL traits of DMS100 and its progeny or derivatives, and/or the mutated fad2 (SEQ ID NO:7) and fad3 (SEQ ID NO:12) genes of DMS100 and its progeny or derivatives. FIGS. 1 and 3.

Example 3

Mutant Allele-specific SNP Markers for fad2 and fad3 Genes

The single nucleotide mutations present in the fad2 and fad3 genes were used as SNP markers to tag the fad2 and fad3 genes for selection of high C18:1 and low C18:3 in canola breeding. Mutant-specific primers (FAD2GM: CGCACCGT-GATGGTTAACGGTTT (SEQ ID NO:5); and FAD3cGM: ATAAATAATGTTGATCTACTTAT (SEQ ID NO:15)) were designed in order to detect mutant alleles of fad2 and fad32 using PCR amplification. The primers were designed such that the mutated base (SNP) was at the 3' end of one of the primers for allele-specific PCR amplification. FIGS. 1 and 3.

The primers specific to fad2 amplified a polymorphic band that was present in DMS100 and DNA bulks for high oleic acid (C18:1), but were absent in Quantum and the DNA bulks for low oleic acid. FIG. 4. This gene-specific marker was tested on a DH population derived from the cross of Quantum and DMS100, where it was found that the allele distribution was highly correlated to high C18:1. FIG. 4; Table 1. The fad3 allele-specific primers also amplified a polymorphic fragment that was present in DMS100, but absent in Quantum. The analysis with the DH population indicated that this allele-specific marker was statistically associated with low C18:3.

FIG. 4; Table 1. Thus, two gene-specific PCR-based markers that directly tag fad2 and fad3 gene mutations were successfully developed. Given the contents of this disclosure, variations or derivatives of the markers disclosed herein (including markers of various types) based for example, on substantial homology over a sufficient number of base pairs, will be readily apparent to one of skill in the art.

TABLE 1

| Genotype | Total plants* | Number of plants rated in each category | | | | ID (%) | CR CALL |
|---|---|---|---|---|---|---|---|
| | | 0 | 1 | 2 | 3 | | |
| DAS 34 | 36 | 36 | 0 | 0 | 0 | 0 | R |
| DAS 35 | 35 | 35 | 0 | 0 | 0 | 0 | R |
| DAS 36 | 36 | 36 | 0 | 0 | 0 | 0 | R |
| DAS 37 | 36 | 36 | 0 | 0 | 0 | 0 | R |
| DAS 38 | 36 | 2 | 0 | 0 | 34 | 94.4 | S |
| DAS 39 | 36 | 36 | 0 | 0 | 0 | 0 | R |
| DAS 40 | 36 | 36 | 0 | 0 | 0 | 0 | R |
| DAS 41 | 36 | 1 | 1 | 3 | 31 | 92.6 | S |
| DAS 42 | 36 | 1 | 0 | 1 | 34 | 96.3 | S |
| DAS 43 | 36 | 36 | 0 | 0 | 0 | 0 | R |
| DAS 44 | 36 | 6 | 6 | 7 | 17 | 65.7 | M |
| DAS 45 | 34 | 33 | 1 | 0 | 0 | 1 | M |
| DAS 46 | 36 | 36 | 0 | 0 | 0 | 0 | R |
| DAS 47 | 36 | 36 | 0 | 0 | 0 | 0 | R |
| DAS 48 | 36 | 36 | 0 | 0 | 0 | 0 | R |
| DAS 49 | 36 | 0 | 3 | 16 | 17 | 79.6 | M |
| DAS 50 | 30 | 30 | 0 | 0 | 0 | 0 | R |
| DAS 51 | 36 | 31 | 1 | 4 | 0 | 8.3 | M |
| DAS 52 | 36 | 18 | 8 | 6 | 4 | 29.6 | M |
| DAS 53 | 36 | 1 | 1 | 6 | 28 | 89.8 | M |
| DAS 54 | 36 | 0 | 0 | 0 | 36 | 100 | S |
| DAS 55 | 36 | 2 | 0 | 0 | 34 | 94.4 | S |
| DAS 56 | 36 | 36 | 0 | 0 | 0 | 0 | R |
| DAS 57 | 36 | 36 | 0 | 0 | 0 | 0 | R |
| DAS 58 | 36 | 3 | 3 | 12 | 18 | 75 | M |
| DAS 59 | 36 | 3 | 2 | 2 | 29 | 86.1 | M |
| DAS 60 | 30 | 30 | 0 | 0 | 0 | 0 | R |
| DAS 61 | 36 | 3 | 4 | 10 | 19 | 75 | M |
| DAS 62 | 30 | 18 | 5 | 4 | 3 | 24.4 | M |
| DAS 63 | 36 | 8 | 11 | 8 | 9 | 50 | M |
| DAS 64 | 36 | 3 | 1 | 16 | 16 | 75 | M |
| DAS 65 | 34 | 34 | 0 | 0 | 0 | 0 | R |
| DAS 66 | 30 | 30 | 0 | 0 | 0 | 0 | R |
| DAS 67 | 36 | 8 | 9 | 7 | 12 | 54.6 | M |
| DAS 68 | 36 | 36 | 0 | 0 | 0 | 0 | R |
| DAS 69 | 33 | 12 | 5 | 8 | 8 | 45.5 | M |
| DAS 70 | 30 | 30 | 0 | 0 | 0 | 0 | R |
| DAS 71 | 36 | 13 | 8 | 9 | 6 | 40.7 | M |
| DAS 72 | 32 | 32 | 0 | 0 | 0 | 0 | R |
| DAS 73 | 34 | 34 | 0 | 0 | 0 | 0 | R |
| DAS 74 | 35 | 34 | 1 | 0 | 0 | 1 | M |

Figure 5:
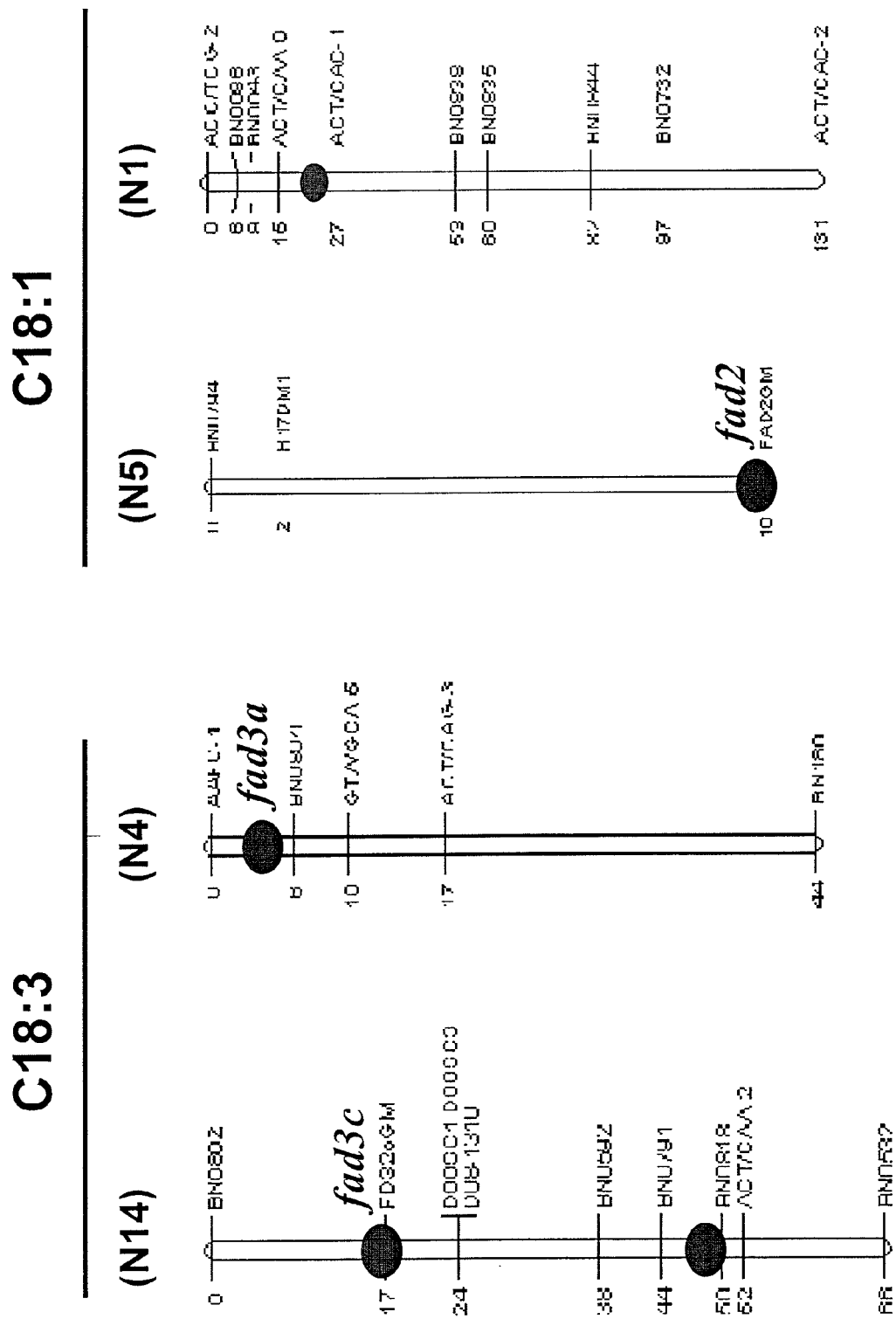
FIG. 5 includes a quantitative trait locus (QTL) map showing one major (N5) and one minor (N1) QTL region for high oleic acid (C18:1), and three QTL regions (N4 and N14) for low linolenic acid (C18:3) detected by markers of the present invention.

Through genetic and QTL mapping using the DH population derived from the cross of Quantum×DMS100, one major (N5) and one minor (N1) QTL region for high C18:1, and three QTL regions (N4 and N14) for low C18:3 were found. FIG. 5. This QTL mapping result is consistent with genetic analyses showing that high C18:1 is controlled by one major gene, and low C18:3 is controlled by multiple genes. The fad2 gene-based marker was located exactly at the mapped location of the major QTL locus for C18:1, supporting the fact that this QTL corresponds to the functional fad2 gene that is affected by the mutation in DMS100. This is also consistent with previous studies demonstrating that the fad2 gene may be located on the linkage group, N5. See Schierholt et al. (2000) Theor. Appl. Genet. 101:897-901. The location of the fad3 gene-based marker matches exactly with the mapped location of one of the major QTL loci for C18:3 on the linkage group 14 (C genome), supporting the conclusion that this QTL is the fad3c (fad3 in the C genome, previously called fad32) gene, and it is affected by the second mutation in DMS100.

Example 4

Production of Breeding Populations

Figure 7:
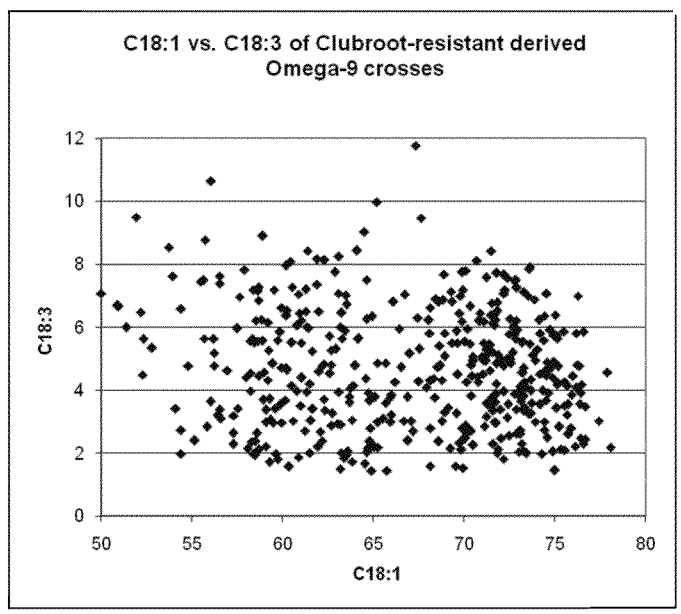
FIG. 7 includes FAME graphs showing the distribution of fatty acid profiles for various plant crosses.

The initial breeding cross involved a HOLL×non-HOLL canola. The $F_1$ was used as a doubled haploid donor, and all of the donor plants were hemizygous for each of the three fad mutants. All of the donor plants were hemizygous for each of the three required fatty acid desaturase mutations. All three genes were predicted to assort independently. Thus, given the population of 457 harvested individuals, it was expected that ⅛ of these individuals (½×½×½) would contain all three FAD markers. Therefore, of the 457 individuals, approximately 57 individuals were expected to contain all three FAD markers that contribute to a HO/LL canola. However, as observed in the FAME analysis shown in FIG. 7, this expectation was not seen in this population.

The distribution of fatty acid profile in the HO/LL×non-HO/LL cross was not what was expected. There were fewer individuals with low C18:3 in this population than what would have been expected, and many more individuals with very low C18:1 composition. 202 individuals produced a C18:1 level of greater than 70%, but only 101 individuals produced a C18:3 level of under 3.0%. Only 41 individuals had the combination of greater than 70% C18:1 and less than 3.0% C18:3. This was lower than the expected number of 57 individuals. Instead of 12% of the individuals containing the HO/LL seed oil profile (as expected), only 9% of the individuals showed this profile.

The effect of combining the two sets of parental material was also investigated. HO/LL parents were crossed to non-HO/LL parents to produce breeding populations. This population produced a large number of DH lines that did not meet HO/LL or standard canola fatty acid profiles, even though the parents were both HO/LL or had standard canola fatty acid profiles (C18-1; C18-3). 88 DH lines produced a C18:1 profile commonly found in non-canola quality materials of less than 60% C18:1. This was an unexpected result, since the genetic composition of the donor plants was hemizygous for all three FAD mutations. A greater production of both C16:0 and C18:2 in these materials was observed as compared to the HO/LL and near-HO/LL types. These non-canola quality types produced a slightly elevated C16:0 level as compared to the HO/LL lines, but the greatest differences between these two classes of lines was the level of linolenic acid (C18:2). Lines containing very low levels of C18:1 had very high levels of C18:2, and also very high levels of C18:3. There were lines with less than 60% C18:1 that had very low levels of C18:3 (less than 2%), representing an interesting combination of genetics that we have not seen in these kinds of crosses before.

Given the genetic expectations of parent lines hemizygous for all three FAD mutations, it would have been predicted that a large proportion of HO/LL lines would exhibit resistance to clubroot. However, the complexity of the fatty acid composition observed in progeny of such plants indicates that it would be difficult to develop HO/LL lines with resistance to clubroot by crossing hemizygous FAD plants.

Figure 8:
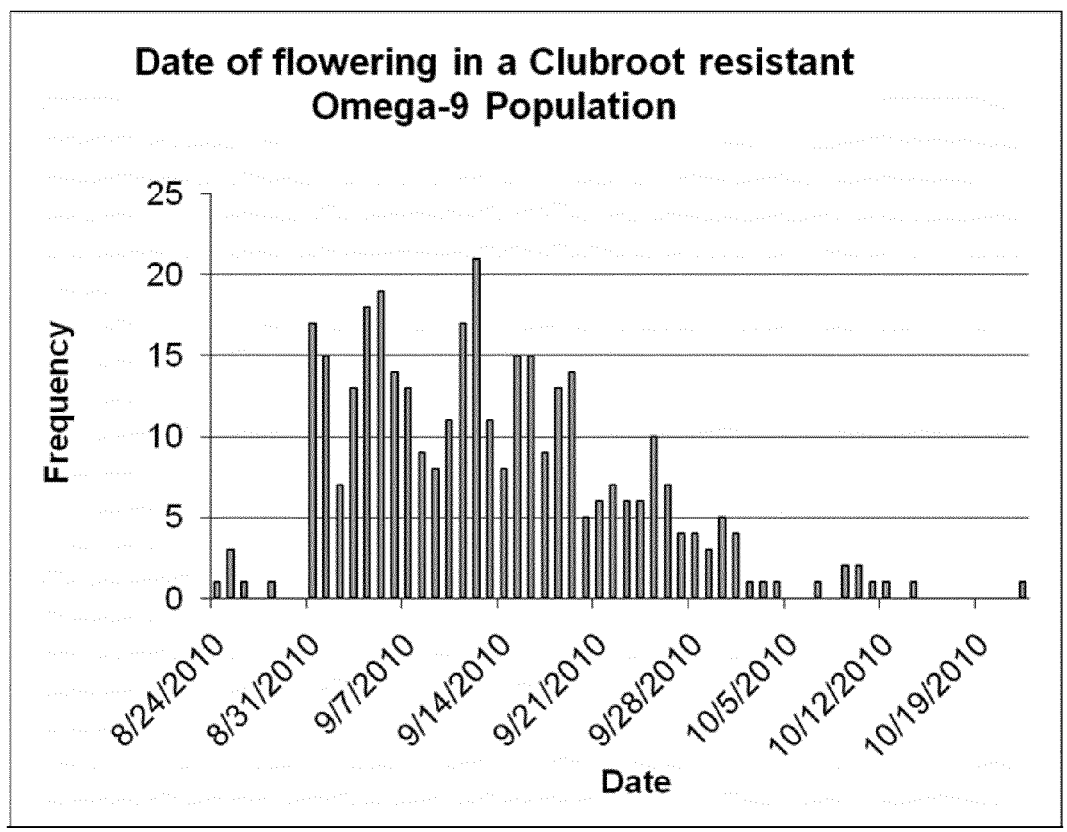
FIG. 8 includes an illustration of the distribution of the flowering date in exemplary clubroot disease resistant, high oleic acid, and low linolenic acid canola plants.
Figure 9:
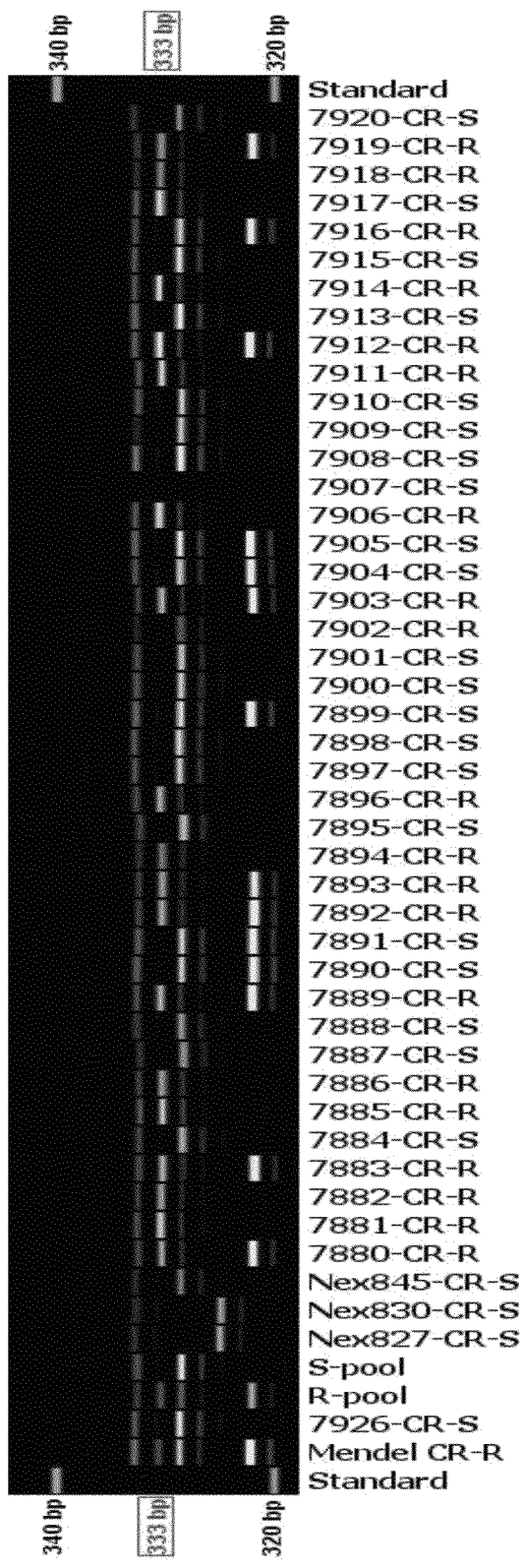
FIG. 9 includes a gel image showing the identification of a molecular marker linked to clubroot disease resistance in canola. The identified marker band linked with clubroot resistant is highlighted in red, and in this case the size of the amplified fragment is 333 bp (33 additional base pairs in total were added to the primers of SEQ ID NOs:18 and 19 (26 bases were added to the 5' end of SEQ ID NO:18, and 7 bases were added to the 5' end of SEQ ID NO:19, as given in SEQ ID NOs:20 and 21, respectively) to facilitate detection using ABI 3130 genetic Analyzer). The clubroot disease reaction of each line tested is provided.

Another complexity observed during the combination of HO/LL and non-HO/LL parents was producing early flowering HO/LL lines in the progeny population. As illustrated in the flowering graph of FIG. 8, the frequency of number of breeding lines was compared to the flowering date. Very few of the breeding lines were early flowering, and there was a tendency for the distribution to be flattened out with more lines exhibiting later flowering. Producing very early flowering, HO/LL, and clubroot resistant lines proved unexpectedly difficult using this parental material. The large differences in flowering were also evident in the resistant lines identified in FIG. 7.

The resistant lines identified in Table 1 (DAS 34 through DAS 74) were planted to make breeding crosses back to a HOLL parent. The resistant lines in Table 1 produced a very large difference in first flowering date from March 19 to April 2. Four of the resistant lines were extremely late flowering, and did not produce flowers until the HOLL parent was out of flower. Notably, the four earliest clubroot-resistant lines to flower in this experiment had only two of the three FAD markers. Two of the four extremely late flowering lines had all three FAD mutants, and two of the extremely late flowering lines had two of the FAD mutants. This indicates the complexity and difficulty of producing clubroot-resistant, early-flowering, and HOLL germplasm in a single *Brassica* line.

Example 5

FAME Analysis

For the 40 separate strains analyzed in Example 3, FAME analysis was conducted to determine the fatty acid content of the strains. The results are presented in Tables 2 and 3 below:

TABLE 2

FAME analysis (C12:0-C18:3)

| Genotype | % Sats | C12:0 | C14:0 | C16:0 | C16:1 | C18:0 | C18:1 | C18:2 | C18:3 |
|---|---|---|---|---|---|---|---|---|---|
| DAS 34 | 8.11 | nd | 0.04 | 4.29 | 0.52 | 2.19 | 73.09 | 12.50 | 3.96 |
| DAS 35 | 7.73 | nd | 0.07 | 4.82 | 0.46 | 1.57 | 62.95 | 21.69 | 5.31 |
| DAS 36 | 7.89 | nd | 0.07 | 4.77 | 0.52 | 1.58 | 68.66 | 15.41 | 5.41 |
| DAS 37 | 8.39 | nd | 0.06 | 4.24 | 0.34 | 2.55 | 72.78 | 9.99 | 5.79 |
| DAS 38 | 9.84 | nd | 0.08 | 5.97 | 0.46 | 2.11 | 64.02 | 18.74 | 4.79 |
| DAS 39 | 7.18 | nd | 0.07 | 4.13 | 0.29 | 1.62 | 64.75 | 21.65 | 3.92 |
| DAS 40 | 7.77 | nd | 0.06 | 3.85 | 0.33 | 2.29 | 77.43 | 8.71 | 3.02 |
| DAS 41 | 7.43 | nd | 0.06 | 4.21 | 0.32 | 1.72 | 75.10 | 9.11 | 5.72 |
| DAS 42 | 6.91 | nd | 0.07 | 4.04 | 0.32 | 1.70 | 71.62 | 15.55 | 3.35 |
| DAS 43 | 6.81 | 0.01 | 0.08 | 4.30 | 0.37 | 1.47 | 71.21 | 14.27 | 4.93 |
| DAS 44 | 7.75 | nd | 0.06 | 4.60 | 0.40 | 1.93 | 75.11 | 11.13 | 3.44 |
| DAS 45 | 7.64 | nd | 0.10 | 5.24 | 0.42 | 1.48 | 61.52 | 26.32 | 2.02 |
| DAS 46 | 7.70 | nd | 0.09 | 5.12 | 0.53 | 1.42 | 65.22 | 13.98 | 9.98 |
| DAS 47 | 7.37 | nd | 0.07 | 4.12 | 0.31 | 1.98 | 73.18 | 14.64 | 2.30 |
| DAS 48 | 7.72 | nd | 0.09 | 4.76 | 0.40 | 1.74 | 69.91 | 12.01 | 7.76 |
| DAS 49 | 7.28 | 0.02 | 0.07 | 3.35 | 0.27 | 2.31 | 76.19 | 8.16 | 5.82 |
| DAS 50 | 7.39 | nd | 0.07 | 4.56 | 0.47 | 1.69 | 69.97 | 18.54 | 1.52 |
| DAS 51 | 7.64 | nd | 0.07 | 4.69 | 0.41 | 1.67 | 70.78 | 14.55 | 4.26 |
| DAS 52 | 6.79 | nd | 0.05 | 3.79 | 0.29 | 1.69 | 74.42 | 10.45 | 5.59 |
| DAS 53 | 6.59 | nd | 0.06 | 4.07 | 0.29 | 1.41 | 73.64 | 11.65 | 5.47 |
| DAS 54 | 8.08 | nd | 0.06 | 4.38 | 0.26 | 2.35 | 65.77 | 22.22 | 1.44 |
| DAS 55 | 7.36 | nd | 0.08 | 4.82 | 0.41 | 1.35 | 69.24 | 18.40 | 2.14 |
| DAS 56 | 7.56 | 0.03 | 0.10 | 3.73 | 0.29 | 2.39 | 73.29 | 11.82 | 4.71 |
| DAS 57 | 6.98 | nd | 0.08 | 4.37 | 0.28 | 1.55 | 58.65 | 24.75 | 7.16 |
| DAS 58 | 7.48 | nd | 0.05 | 4.65 | 0.37 | 1.62 | 74.66 | 11.19 | 3.91 |
| DAS 59 | 6.49 | nd | 0.08 | 4.51 | 0.32 | 1.19 | 71.51 | 11.15 | 8.43 |
| DAS 60 | 7.18 | nd | 0.09 | 4.15 | 0.36 | 1.71 | 70.11 | 11.98 | 7.80 |
| DAS 61 | 6.59 | nd | 0.05 | 3.93 | 0.25 | 1.45 | 64.19 | 20.84 | 5.65 |
| DAS 62 | 6.39 | nd | 0.05 | 3.44 | 0.23 | 1.64 | 69.86 | 19.00 | 2.12 |
| DAS 63 | 7.00 | nd | 0.07 | 3.33 | 0.24 | 2.19 | 75.71 | 10.52 | 4.14 |
| DAS 64 | 7.95 | nd | 0.06 | 4.30 | 0.29 | 2.20 | 64.63 | 17.37 | 7.51 |
| DAS 65 | 7.52 | nd | 0.07 | 4.27 | 0.36 | 1.80 | 61.40 | 19.72 | 8.43 |
| DAS 66 | 6.64 | nd | 0.07 | 3.92 | 0.34 | 1.65 | 73.70 | 12.85 | 4.33 |
| DAS 67 | 7.33 | nd | 0.06 | 4.17 | 0.34 | 1.97 | 75.95 | 10.35 | 3.86 |
| DAS 68 | 7.21 | nd | 0.07 | 4.03 | 0.33 | 1.90 | 72.56 | 12.63 | 4.99 |
| DAS 69 | 7.32 | nd | 0.06 | 4.31 | 0.42 | 1.72 | 72.42 | 12.31 | 4.99 |
| DAS 70 | 7.01 | nd | 0.07 | 4.04 | 0.31 | 1.89 | 73.04 | 15.43 | 2.04 |
| DAS 71 | 7.49 | 0.01 | 0.08 | 4.91 | 0.34 | 1.44 | 54.41 | 28.79 | 6.59 |
| DAS 72 | 7.32 | nd | 0.06 | 4.66 | 0.36 | 1.53 | 71.69 | 12.04 | 6.42 |
| DAS 73 | 7.59 | nd | 0.07 | 5.11 | 0.41 | 1.40 | 58.09 | 29.38 | 2.16 |

TABLE 3

FAME analysis (C20:0-C24:1)

| Genotype | C20:0 | C20:1 | C20:2 | C22:0 | C22:1 | C24:0 | C24:1 |
|---|---|---|---|---|---|---|---|
| DAS 34 | 0.78 | 1.27 | 0.07 | 0.44 | nd | 0.36 | 0.18 |
| DAS 35 | 0.63 | 1.23 | 0.09 | 0.42 | nd | 0.23 | 0.17 |
| DAS 36 | 0.70 | 1.46 | 0.08 | 0.51 | nd | 0.27 | 0.25 |
| DAS 37 | 0.84 | 1.31 | 0.06 | 0.40 | nd | 0.30 | 0.16 |
| DAS 38 | 0.82 | 1.23 | 0.07 | 0.49 | nd | 0.37 | 0.26 |
| DAS 39 | 0.62 | 1.47 | 0.11 | 0.41 | nd | 0.33 | 0.16 |
| DAS 40 | 0.81 | 1.35 | 0.05 | 0.45 | 0.02 | 0.32 | 0.15 |
| DAS 41 | 0.74 | 1.50 | 0.05 | 0.49 | nd | 0.20 | 0.14 |

TABLE 3-continued

FAME analysis (C20:0-C24:1)

| Genotype | C20:0 | C20:1 | C20:2 | C22:0 | C22:1 | C24:0 | C24:1 |
|---|---|---|---|---|---|---|---|
| DAS 42 | 0.61 | 1.35 | 0.08 | 0.33 | nd | 0.17 | 0.14 |
| DAS 43 | 0.54 | 1.38 | 0.06 | 0.29 | 0.02 | 0.10 | 0.13 |
| DAS 44 | 0.67 | 1.21 | 0.04 | 0.33 | 0.02 | 0.17 | 0.12 |
| DAS 45 | 0.47 | 0.98 | 0.07 | 0.22 | nd | 0.13 | 0.14 |
| DAS 46 | 0.55 | 1.43 | 0.06 | 0.33 | 0.03 | 0.19 | 0.21 |
| DAS 47 | 0.71 | 1.26 | 0.07 | 0.36 | nd | 0.14 | 0.11 |
| DAS 48 | 0.63 | 1.28 | 0.06 | 0.35 | nd | 0.15 | 0.12 |
| DAS 49 | 0.84 | 1.44 | 0.06 | 0.43 | 0.02 | 0.25 | 0.14 |
| DAS 50 | 0.57 | 1.06 | 0.06 | 0.29 | nd | 0.20 | 0.23 |
| DAS 51 | 0.67 | 1.35 | 0.06 | 0.38 | 0.02 | 0.16 | 0.15 |
| DAS 52 | 0.70 | 1.56 | 0.06 | 0.42 | nd | 0.14 | 0.13 |
| DAS 53 | 0.57 | 1.40 | 0.06 | 0.34 | 0.02 | 0.15 | 0.16 |
| DAS 54 | 0.76 | 1.24 | 0.08 | 0.38 | 0.01 | 0.15 | 0.17 |
| DAS 55 | 0.55 | 1.34 | 0.08 | 0.34 | 0.02 | 0.22 | 0.20 |
| DAS 56 | 0.80 | 1.34 | 0.07 | 0.37 | nd | 0.15 | 0.12 |
| DAS 57 | 0.54 | 1.12 | 0.08 | 0.31 | nd | 0.13 | 0.13 |
| DAS 58 | 0.60 | 1.38 | 0.05 | 0.34 | 0.03 | 0.21 | 0.11 |
| DAS 59 | 0.42 | 1.17 | 0.06 | 0.21 | nd | 0.09 | 0.14 |
| DAS 60 | 0.64 | 1.47 | 0.07 | 0.34 | nd | 0.26 | 0.21 |
| DAS 61 | 0.59 | 1.42 | 0.09 | 0.36 | 0.02 | 0.21 | 0.18 |
| DAS 62 | 0.67 | 1.42 | 0.09 | 0.41 | 0.02 | 0.18 | 0.12 |
| DAS 63 | 0.80 | 1.51 | 0.07 | 0.41 | nd | 0.21 | 0.16 |
| DAS 64 | 0.79 | 1.22 | 0.07 | 0.42 | 0.01 | 0.18 | 0.16 |
| DAS 65 | 0.70 | 1.46 | 0.08 | 0.45 | 0.03 | 0.21 | 0.15 |
| DAS 66 | 0.58 | 1.27 | 0.06 | 0.29 | nd | 0.12 | 0.12 |
| DAS 67 | 0.66 | 1.26 | 0.04 | 0.32 | nd | 0.15 | 0.10 |
| DAS 68 | 0.68 | 1.30 | 0.06 | 0.35 | 0.02 | 0.19 | 0.13 |
| DAS 69 | 0.66 | 1.40 | 0.07 | 0.37 | nd | 0.19 | 0.17 |
| DAS 70 | 0.61 | 1.23 | 0.07 | 0.29 | nd | 0.10 | 0.09 |
| DAS 71 | 0.54 | 1.26 | 0.10 | 0.32 | 0.06 | 0.19 | 0.16 |
| DAS 72 | 0.61 | 1.24 | 0.06 | 0.37 | nd | 0.09 | 0.14 |
| DAS 73 | 0.52 | 1.25 | 0.08 | 0.30 | nd | 0.20 | 0.17 |

Example 6

Selection of Herbicide Tolerance

Approximately 1000 BC1 generation individuals (from backcrossing Mendel×HO/LL/rest/gly individuals to imidazolinone- and glyphosate-resistant inbreds) were surveyed for the fertility restorer gene. It was determined that approximately 156 BC1 individuals were homozygous, 469 were hemizygous, and 370 individuals were wild-type for the fertility restorer. The proportions of fertile (homozygous and hemizygous) individuals were lower than expected given the expected rations of 50% homozygous and 50% hemizygous for the fertility restorer; the actual results were 625 fertile:469 sterile, a significant departure from the expected ratio.

Additional assays were conducted on fertile (homozygous and hemizygous) plants to determine the presence of glyphosate resistance. The 327 glyphosate resistance negative BC1 plants were used for imidazolinone resistance breeding. The imidazolinone resistant types produced an approximate ratio of 1:1 homozygous:hemizygous for each of three FAD genes (173:150 for FAD2, 144:177 for FAD3A, and 174:153 for FAD3C) and, of the resulting plants, 83 were homozygous for the restorer gene and 244 were hemizygous. Individual glyphosate resistance negative lines were compared for the presence of the FAD genes, as well as the restorer gene, and plants identified as homozygous for two of the three FAD genes as well as homozygous for the restorer gene were planted in greenhouse pots for selection for "earliness to flower."

Days to flower under greenhouse conditions were determined for each plant, and the earliest flowering plants with two or three FAD genes and the restorer were individually bag-selfed to produce pure BC1S1 seed. Once harvested, small seed samples were tested to verify the fatty acid profiles of the seed oil. The oleic acid (C18:1) content in these samples ranged from 63.34% to 77.34%. Linolenic acid (C18:3) content ranged from 5.81% to 1.32%, and saturated fatty acid composition ranged from 9.64% to 6.49%. Remnant seed of the 20 earliest flowering BC1S1 imidazolinone resistant, high oleic, low linolenic, restorer gene lines were tested, and all were determined to carry clubroot disease resistance.

Example 7

Markers Linked to Clubroot Disease Resistance

The clubroot disease-resistant B. napus cultivar, Mendel, was used to produce of series of crosses into a HO/LL B. napus inbred containing a fertility restoration gene (restr) and glyphosate resistance (gly). The resulting $F_1$ progeny were backcrossed to imidazolinone- and glyphosate-resistant inbreds, with selection for HO/LL, fertility restoration, and herbicide tolerance. The $F_1$ plants were intermediate for growth habit and required low temperature vernalization to induce flowering. Molecular marker characterization was used to combine herbicide tolerance, seed oil profiles and fertility restoration to identify $F_1$ individuals to use as crossing parents to develop the BC1 generations. Subsequent to making the BC1 generation, clubroot resistance was determined using a biological assay that indicated that the clubroot disease resistance was transferred to the HO/LL parent types. Table 4 provides the results of testing for clubroot resistance for multiple plants from 40 separate strains. The plants were ranked in categories ranging from 0 (resistant) to 3 (susceptible). The strain as a whole was then assigned a letter grade from R (resistant), M (mixed resistance), and S (susceptible).

TABLE 4

Results of testing for clubroot disease resistance in 40 separate canola strains (multiple plants)

| Genotype | Total plants* | Number of plants rated in each category | | | | ID (%) | Clubroot Resistance |
| --- | --- | --- | --- | --- | --- | --- | --- |
| | | 0 | 1 | 2 | 3 | | |
| DAS 34 | 36 | 36 | 0 | 0 | 0 | 0 | R |
| DAS 35 | 35 | 35 | 0 | 0 | 0 | 0 | R |
| DAS 36 | 36 | 36 | 0 | 0 | 0 | 0 | R |
| DAS 37 | 36 | 36 | 0 | 0 | 0 | 0 | R |
| DAS 38 | 36 | 2 | 0 | 0 | 34 | 94.4 | S |
| DAS 39 | 36 | 36 | 0 | 0 | 0 | 0 | R |
| DAS 40 | 36 | 36 | 0 | 0 | 0 | 0 | R |
| DAS 41 | 36 | 1 | 1 | 3 | 31 | 92.6 | S |
| DAS 42 | 36 | 1 | 0 | 1 | 34 | 96.3 | S |
| DAS 43 | 36 | 36 | 0 | 0 | 0 | 0 | R |
| DAS 44 | 36 | 6 | 6 | 7 | 17 | 65.7 | M |
| DAS 45 | 34 | 33 | 1 | 0 | 0 | 1 | M |
| DAS 46 | 36 | 36 | 0 | 0 | 0 | 0 | R |
| DAS 47 | 36 | 36 | 0 | 0 | 0 | 0 | R |
| DAS 48 | 36 | 36 | 0 | 0 | 0 | 0 | R |
| DAS 49 | 36 | 0 | 3 | 16 | 17 | 79.6 | M |
| DAS 50 | 30 | 30 | 0 | 0 | 0 | 0 | R |
| DAS 51 | 36 | 31 | 1 | 4 | 0 | 8.3 | M |
| DAS 52 | 36 | 18 | 8 | 6 | 4 | 29.6 | M |
| DAS 53 | 36 | 1 | 1 | 6 | 28 | 89.8 | M |
| DAS 54 | 36 | 0 | 0 | 0 | 36 | 100 | S |
| DAS 55 | 36 | 2 | 0 | 0 | 34 | 94.4 | S |
| DAS 56 | 36 | 36 | 0 | 0 | 0 | 0 | R |
| DAS 57 | 36 | 36 | 0 | 0 | 0 | 0 | R |
| DAS 58 | 36 | 3 | 3 | 12 | 18 | 75 | M |
| DAS 59 | 36 | 3 | 2 | 2 | 29 | 86.1 | M |
| DAS 60 | 30 | 30 | 0 | 0 | 0 | 0 | R |
| DAS 61 | 36 | 3 | 4 | 10 | 19 | 75 | M |
| DAS 62 | 30 | 18 | 5 | 4 | 3 | 24.4 | M |
| DAS 63 | 36 | 8 | 11 | 8 | 9 | 50 | M |
| DAS 64 | 36 | 3 | 1 | 16 | 16 | 75 | M |
| DAS 65 | 34 | 34 | 0 | 0 | 0 | 0 | R |
| DAS 66 | 30 | 30 | 0 | 0 | 0 | 0 | R |
| DAS 67 | 36 | 8 | 9 | 7 | 12 | 54.6 | M |
| DAS 68 | 36 | 36 | 0 | 0 | 0 | 0 | R |
| DAS 69 | 33 | 12 | 5 | 8 | 8 | 45.5 | M |
| DAS 70 | 30 | 30 | 0 | 0 | 0 | 0 | R |
| DAS 71 | 36 | 13 | 8 | 9 | 6 | 40.7 | M |
| DAS 72 | 32 | 32 | 0 | 0 | 0 | 0 | R |
| DAS 73 | 34 | 34 | 0 | 0 | 0 | 0 | R |
| DAS 74 | 35 | 34 | 1 | 0 | 0 | 1 | M |

A 3-way cross of Mendel (clubroot resistant) HO/LL inbred with a clubroot disease-susceptible B. napus inbred was made. Forty DH lines originated from a $F_1$ generation plant of this 3-way cross were screened for clubroot disease resistance using the biological assay. Table 5. These selected DH lines, two parental lines, and three canola varieties (NEX 827, NEX 830, and NEX 845) were grown, and leaf tissue was collected from each. The collected leaf tissues were freeze-dried and ground for DNA extractions.

TABLE 5

DH lines used to identify clubroot molecular markers.

| Loc Seq# | Geno_Id | Source ID |
| --- | --- | --- |
| 7880 | 140227 | BS09PS000170.005 |
| 7881 | 140243 | BS09PS000170.021 |
| 7882 | 140251 | BS09PS000170.029 |
| 7883 | 145442 | BS09PS000170.120 |
| 7884 | 145506 | BS09PS000170.184 |
| 7885 | 145551 | BS09PS000170.229 |
| 7886 | 145557 | BS09PS000170.235 |
| 7887 | 145645 | BS09PS000170.323 |
| 7888 | 145666 | BS09PS000170.344 |
| 7889 | 145721 | BS09PS000170.399 |
| 7890 | 145733 | BS09PS000170.411 |
| 7891 | 145768 | BS09PS000170.446 |
| 7892 | 145776 | BS09PS000170.454 |
| 7893 | 145779 | BS09PS000170.457 |
| 7894 | 145784 | BS09PS000170.462 |
| 7895 | 145790 | BS09PS000170.468 |
| 7896 | 145791 | BS09PS000170.469 |
| 7897 | 145810 | BS09PS000170.488 |
| 7898 | 145813 | BS09PS000170.491 |
| 7899 | 145814 | BS09PS000170.492 |
| 7900 | 145842 | BS09PS000170.520 |
| 7901 | 145850 | BS09PS000170.528 |
| 7902 | 145853 | BS09PS000170.531 |
| 7903 | 145860 | BS09PS000170.538 |
| 7904 | 145863 | BS09PS000170.541 |
| 7905 | 145864 | BS09PS000170.542 |
| 7906 | 145882 | BS09PS000170.560 |
| 7907 | 145946 | BS09PS000170.624 |
| 7908 | 145978 | BS09PS000170.656 |
| 7909 | 146007 | BS09PS000170.685 |
| 7910 | 146034 | BS09PS000170.712 |
| 7911 | 146037 | BS09PS000170.715 |
| 7912 | 146038 | BS09PS000170.716 |
| 7913 | 146039 | BS09PS000170.717 |
| 7914 | 146043 | BS09PS000170.721 |
| 7915 | 146049 | BS09PS000170.727 |
| 7916 | 146058 | BS09PS000170.736 |
| 7917 | 146074 | BS09PS000170.752 |
| 7918 | 146075 | BS09PS000170.753 |
| 7919 | 146091 | BS09PS000170.769 |
| 7920 | 21641 | BS08PS000120.001 |

DNA was extracted from freeze-dried ground leaf tissues using the Qiagen™ Mini Plant DNA extraction kit according to the kit's instructions. Extracted DNA samples were quantified using NanoDrop™ 8000, and brought to the concentration of 5 ng/μL by dilution with ultra pure water. Two separate bulked DNA samples were formulated using equal amounts of DNA from 5 clubroot resistant DH lines (the "R-pool") (DH lines 140227, 145776, 145853, 145882 and 146058) and 5 susceptible DH lines (the "S-pool") (DH lines 145506, 145645, 145666, 145842, 145850).

These two bulked DNA samples along with parental DNA samples were used to identify SSR markers (Simple Sequence Repeats markers) linked with clubroot disease resistant in canola using bulked segregant analysis approach: We employed a bulked segregation analysis (BSA) approach utilizing the R-pool, the S-pool, and DNA samples from their respective parental lines, with Simple Sequence Repeat (SSR) molecular markers. Then, SSR markers identified as polymorphic between the two bulked DNA samples and parental lines were tested with 40 individual DH lines with known clubroot disease resistance.

The two bulked DNA samples and two parental lines were screened with a total of 713 SSR M13-labeled primer pairs and an ABI 3130 Genetic Analyzer, to identify polymorphic markers between resistant and susceptible pools, as well as parental DNA. Screening was conducted by preparing PCR reactions with primers having the sequences set forth as SEQ IDs 20, 21, and 22(FAM-labeled); HotMaster™ Taq polymerase; and HotMaster™ reaction buffer. PCR reactions were performed with 1 cycle at 95° C. for 3 minutes; 4 cycles of touch down profile consisting of 94° C. for 30 seconds, 56° C. for 50 seconds (−2° C./cycle), and 72° C. for 55 seconds; 24 cycles of 94° C. for 30 seconds, 51° C. for 50 seconds, and 72° C. for 55 seconds; 1 cycle of 72° C. for 10 minutes; and a final incubation at 8° C. until completion. Completed PCR reactions were diluted (7 µL reaction into 100 µL H₂O), and 4 µL of the diluted PCR product was mixed with SSR running buffer (10.8 µL HiDi Formamide and 0.2 µL Gene Scan 600 LIZ standard DNA) and transferred to a plate for use in an ABI 3130×1 Genetic Analyzer. The plates were then quick spun briefly (max 500 rpm for a few seconds), denatured for 5 minutes at 95° C., and cooled on ice. The plates were quick spun again to ensure that all liquid was at the bottom of each well and there were no air bubbles. The prepared plates were then fitted into a plate assembly and loaded into the ABI 3130xl Genetic Analyzer. Data were analyzed using GeneMapper™ software.

42 of the 713 SSR primer pairs screened were polymorphic in DNA amplifications between the resistant DNA pool (R-pool) and the susceptible DNA pool (S-pool), and the observed polymorphisms were consistent with the resistant parent (Mendel) and susceptible inbred parent. These 42 SSR markers were used to screen the forty individual DH lines, the parental varieties, NEX 827, NEX 830, and NEX 845 to determine the linkage between marker and the clubroot resistant phenotype.

The bulked segregant analysis identified one SSR primer pair (BN1810) producing an amplification of a 333 bp DNA fragment closely associated with the clubroot disease resistant phenotype. Table 6.

BN1810 SSR Marker

```
BN1810-DAS-M13F:
                                   (SEQ ID NO: 20)
CACGACGTTGTAAAACGACGGCCAGTTTCTCCGACCAAAGCTGTTT

BN 1810-Tailed R:
                                   (SEQ ID NO: 21)
GTTTCTTAAGGAGCTGGATTCACATGG M13-6FAM (Fluorescently labeled primer):
                                   (SEQ ID NO: 22)
6FAM-CACGACGTTGTAAAACGA
```

Except for two misclassifications, this marker accurately predicts the clubroot disease reaction of tested canola lines. Data from Table 6 demonstrates 19 resistant individuals, 13 susceptible individuals, and 6 individuals classified as moderately resistant. This marker was also tested with another DH population that was derived from Mendel as a resistant parent, and the marker predicted the expected segregation ratio of resistant to susceptible individuals. The individuals assessed in this other DH population were not from homozygous parents, so some segregation was expected.

TABLE 6

Clubroot disease reaction and marker alleles of BN1810 SSR primer pair for the individual DH lines, parental lines and DAS canola verities used to determine the linkage relationship. Marker allele classifying phenotypes correctly are highlighted in gray and misclassified ones are in bold text (yellow).

| Sample ID | Clubroot phenotype | BN1810 SSR marker alleles | | | |
|---|---|---|---|---|---|
| | | Allele 1 | Allele 2 | Allele 3 | Allele 3* |
| Mendel | R | 325 | | 331 | 333 |
| 7926 | S | | | 331 | |
| R-Pool | | 325 | | 331 | 333 |
| S-Pool | | | | 331 | |
| Nex827 | S | | 327 | | |
| Nex830 | S | | 327 | | |
| Nex845 | S | | | 331 | |
| 140227 | R | 325 | | | 333 |
| 140243 | R | | | | 333 |
| 140251 | R | | | | 333 |
| 145442 | R | 325 | | | 333 |
| 145506 | S | | | 331 | |
| 145551 | R | | | | 333 |
| 145557 | R | | | | 333 |
| 145645 | S | | | 331 | |
| 145666 | S | | | 331 | |
| 145721 | R | 325 | | | 333 |
| 145733 | S | | 325 | 331 | |
| 145768 | R | 325 | | 331 | |
| 145776 | R | 325 | | | 333 |
| 145779 | R | 325 | | | 333 |
| 145784 | R | | | | 333 |
| 145790 | S | | | 331 | |
| 145791 | R | | | | 333 |
| 145810 | MR | | | 331 | |
| 145813 | S | | | 331 | |
| 145814 | S | 325 | | 331 | |
| 145842 | S | | | 331 | |
| 145850 | S | | | 331 | |
| 145853 | R | | | 331 | |
| 145860 | R | 325 | | | 333 |
| 145863 | S | 325 | | 331 | |
| 145864 | S | 325 | | 331 | |
| 145882 | R | | | | 333 |
| 145946 | S | | | | |
| 145978 | MR | | | 331 | |
| 146007 | MR | | | 331 | |
| 146034 | S | | | 331 | |
| 146037 | R | | | | 333 |
| 146038 | R | 325 | | | 333 |
| 146039 | MR | | | 331 | |
| 146043 | R | | | | 333 |
| 146049 | MR | | | 331 | |
| 146058 | R | 325 | | 331 | |
| 146074 | MR | | | | 333 |
| 146075 | R | | | | 333 |
| 146091 | R | 325 | | | 333 |

*The allele identified linked with clubroot disease resistant and contributed from clubroot resistant parental line, Mendel.

Example 8

Identification of Clubroot Disease Resistance Gene(s)

The region of genomic *B. napus* DNA amplified by the BN1810 SSR primer pair is sequenced. The sequence of the amplified region is used to probe genomic databases for identification of the gene comprising the BN1810 SSR marker.

The gene comprising the BN1810 SSR marker is identified, and this gene is determined to be a source of clubroot disease resistance.

The identified clubroot disease resistance gene is located in a *Brassica* genome, and markers that are near enough to the gene to be linked during meiosis are identified. The identified markers are screened in $F_1$ populations of crosses between clubroot disease resistant and susceptible varieties to further identify a subset of the markers that are polymorphic, and thus are useful as markers of the source of clubroot disease resistance represented by the BN1810 SSR marker. Some markers in this subset may be more closely linked to clubroot disease resistance than the BN1810 SSR marker.

Genomic DNA is isolated from the provided varieties, and the isolated DNA is probed using the BN1810 SSR primer pair. If amplification of the sequence of isolated DNA between the sequences corresponding to the BN1810 SSR primer pair demonstrates the presence of the marker, the data is evidence that the source of potential clubroot resistance is allelic to the source present in Mendel.

The provided varieties are each crossed with a clubroot disease susceptible line to produce an $F_1$ population. Doubled haploid (DH) lines are produced from this $F_1$ population, and the lines are screened for clubroot disease resistance using a biological assay. The selected DH lines, the two parental lines, and Mendel are grown, and plant tissue is collected from each. DNA is extracted from the collected plant tissues. Extracted DNA samples are quantified, and bulked DNA samples are formulated from clubroot resistant DH lines and clubroot susceptible DH lines.

The bulked DNA samples along with parental DNA samples are used in a bulked segregant analysis approach to determine whether the BN1810 SSR marker is polymorphic between clubroot disease resistant and susceptible DNA pools, parents, and DH lines. If the marker is polymorphic, the data is consistent with the hypothesis that the source of potential clubroot resistance is allelic to the source present in Mendel.

While certain exemplary embodiments have been described herein, those of ordinary skill in the art will recognize and appreciate that many additions, deletions, and modifications to the exemplary embodiments may be made without departing from the scope of the following claims. In addition, features from one embodiment may be combined with features of another embodiment.

The invention claimed is:

1. A method for selecting a *Brassica napus* plant comprising a DNA sequence contributing to clubroot disease resistance in *Brassica napus*, the method comprising:
   isolating genomic DNA from a *B. napus* plant; and
   screening the isolated genomic DNA for a nucleic acid molecular short sequence repeat (SSR) marker comprising a polynucleotide that is amplified in a polymerase chain reaction by the primers of SEQ ID NO:16 and SEQ ID NO:17 and is 300 nucleotides in length;
   selecting a plant comprising a DNA sequence contributing to clubroot disease resistance in *Brassica napus* if the plant comprises the SSR marker; and
   cultivating the selected plant.

2. A method for introducing clubroot disease resistance in a *Brassica* plant, the method comprising:
   crossing the selected plant of claim 1, with a second *Brassica* plant, to generate F$_1$ *Brassica* plants;
   selecting the F$_1$ *Brassica* plant, using marker-assisted selection to identify an F$_1$ *Brassica* plant comprising a polynucleotide 300 nucleotides in length that is amplified by the primers of SEQ ID NO:16 and SEQ ID NO:17 in a polymerase chain reaction; and
   propagating the identified F$_1$ *Brassica* plant, thereby introducing clubroot disease resistance in a *Brassica* plant.

3. A method for selecting a *Brassica napus* plant comprising a DNA sequence contributing to clubroot disease resistance in *Brassica napus*, the method comprising:
   isolating DNA from a *B. napus* plant;
   amplifying a genomic sequence utilizing the primers of SEQ ID NO:20 and SEQ ID NO:21;
   determining the size of the amplified sequence; and
   selecting a plant whose genomic DNA produced an amplified product of 333 base pairs, wherein said plant comprises a DNA sequence that contributes to clubroot disease resistance; and cultivating the selected plant.

* * * * *

```
SEQUENCE LISTING

<160> NUMBER OF SEQ ID NOS: 22

<210> SEQ ID NO 1
<211> LENGTH: 24
<212> TYPE: DNA
<213> ORGANISM: Brassica napus

<400> SEQUENCE: 1
caatccctcg ctctttctcc tacc                                          24

<210> SEQ ID NO 2
<211> LENGTH: 24
<212> TYPE: DNA
<213> ORGANISM: Brassica napus

<400> SEQUENCE: 2
cctttcttgt caccttccct gtcc                                          24

<210> SEQ ID NO 3
<211> LENGTH: 20
<212> TYPE: DNA
<213> ORGANISM: Brassica napus

<400> SEQUENCE: 3
gaggcttgga cgaccacttg                                               20

<210> SEQ ID NO 4
<211> LENGTH: 20
<212> TYPE: DNA
<213> ORGANISM: Brassica napus

<400> SEQUENCE: 4
gactggacca acgaggaatg                                               20

<210> SEQ ID NO 5
<211> LENGTH: 23
<212> TYPE: DNA
<213> ORGANISM: Brassica napus

<400> SEQUENCE: 5
```
cgcaccgtga tggttaacgg ttt                                                23

<210> SEQ ID NO 6
<211> LENGTH: 22
<212> TYPE: DNA
<213> ORGANISM: Brassica napus

<400> SEQUENCE: 6
acaggtgatg cgccacgtgc gt                                                 22

<210> SEQ ID NO 7
<211> LENGTH: 985
<212> TYPE: DNA
<213> ORGANISM: Brassica napus

<400> SEQUENCE: 7
caatccctcg ctctttctcc tacctcatct gggacatcat catagcctcc tgcttctact         60
acgtcgccac cacttacttc cctctcctcc ctcaccctct ctcctacttc gcctggcctc        120
tctactgggc ctgccagggc tgcgtcctaa ccggcgtctg ggtcatagcc acgagtgcg         180
gccaccacgc cttcagcgac taccagtggc tggacgacac cgtcggcctc atcttccact        240
ccttcctcct cgtcccttac ttctcctgga agtacagtca tcgacgccac cattccaaca        300
ctggctccct cgagagagac gaagtgtttg tccccaagaa gaagtcagac atcaagtggt        360
acggcaagta cctcaacaac cctttgggac gcaccgtgat gttaacggtt agttcactc         420
tcggctggcc tttgtactta gccttcaacg tctcggggag accttacgac ggcggcttcg        480
cttgccattt ccaccccaac gctcccatct acaacgaccg tgagcgtctc cagatataca        540
tctccgacgc tggcatcctc gccgtctgct acggtctcta ccgctacgct gctgtccaag        600
gagttgcctc gatggtctgc ttctacggag ttcctcttct gattgtcaac gggttcttag        660
ttttgatcac ttacttgcag cacacgcatc cttccctgcc tcactatgac tcgtctgagt        720
gggattggtt gaggggagct ttggccaccg ttgacagaga ctacggaatc ttgaacaagg        780
tcttccacaa tatccggac acgcacgtgg cgcatcacct gttctcgacc atgccgcatt         840
atcatgcgat ggaagctacg aaggcgataa agccgatact gggagagtat tatcagttcg        900
atgggacgcc ggtggttaag gcgatgtgga gggaggcgaa ggagtgtatc tatgtggaac        960
cggacaggga aggtgacaag aaagg                                              985

<210> SEQ ID NO 8
<211> LENGTH: 136
<212> TYPE: PRT
<213> ORGANISM: Brassica napus

<400> SEQUENCE: 8

Ile Pro Arg Ser Phe Ser Tyr Leu Ile Trp Asp Ile Ile Ile Ala Ser
1               5                   10                  15

Cys Phe Tyr Tyr Val Ala Thr Thr Tyr Phe Pro Leu Pro His Pro
            20                  25                  30

Leu Ser Tyr Phe Ala Trp Pro Leu Tyr Trp Ala Cys Gln Gly Cys Val
        35                  40                  45

Leu Thr Gly Val Trp Val Ile Ala His Glu Cys Gly His His Ala Phe
    50                  55                  60

Ser Asp Tyr Gln Trp Leu Asp Asp Thr Val Gly Leu Ile Phe His Ser
65                  70                  75                  80

Phe Leu Leu Val Pro Tyr Phe Ser Trp Lys Tyr Ser His Arg Arg His
                85                  90                  95

```
His Ser Asn Thr Gly Ser Leu Glu Arg Asp Glu Val Phe Val Pro Lys
        100                 105                 110

Lys Lys Ser Asp Ile Lys Trp Tyr Gly Lys Tyr Leu Asn Asn Pro Leu
        115                 120                 125

Gly Arg Thr Val Met Leu Thr Val
        130                 135

<210> SEQ ID NO 9
<211> LENGTH: 985
<212> TYPE: DNA
<213> ORGANISM: Brassica napus

<400> SEQUENCE: 9
caatccctcg ctctttctcc tacctcatct gggacatcat catagcctcc tgcttctact      60
acgtcgccac cacttacttc cctctcctcc ctcaccctct ctcctacttc gcctggcctc     120
tctactgggc ctgccagggc tgcgtcctaa ccggcgtctg ggtcatagcc acgagtgcg      180
gccaccacgc cttcagcgac taccagtggc tggacgacac cgtcggcctc atcttccact     240
ccttcctcct cgtcccttac ttctcctgga agtacagtca tcgacgccac cattccaaca     300
ctggctccct cgagagagac gaagtgtttg tccccaagaa gaagtcagac atcaagtggt     360
acggcaagta cctcaacaac cctttgggac gcaccgtgat gttaacggtt cagttcactc     420
tcggctggcc tttgtactta gccttcaacg tctcggggag accttacgac ggcggcttcg     480
cttgccattt ccaccccaac gctcccatct acaacgaccg tgagcgtctc cagatataca     540
tctccgacgc tggcatcctc gccgtctgct acggtctcta ccgctacgct gctgtccaag     600
gagttgcctc gatggtctgc ttctacggag ttcctcttct gattgtcaac gggttcttag     660
ttttgatcac ttacttgcag cacacgcatc cttccctgcc tcactatgac tcgtctgagt     720
gggattggtt gaggggagct ttggccaccg ttgacagaga ctacggaatc ttgaacaagg     780
tcttccacaa tatcacggac acgcacgtgg cgcatcacct gttctcgacc atgccgcatt     840
atcatgcgat ggaagctacg aaggcgataa agccgatact gggagagtat tatcagttcg     900
atgggacgcc ggtggttaag gcgatgtgga gggaggcgaa ggagtgtatc tatgtggaac     960
cggacaggga aggtgacaag aaagg                                           985

<210> SEQ ID NO 10
<211> LENGTH: 327
<212> TYPE: PRT
<213> ORGANISM: Brassica napus

<400> SEQUENCE: 10

Ile Pro Arg Ser Phe Ser Tyr Leu Ile Trp Asp Ile Ile Ala Ser
1               5                   10                  15

Cys Phe Tyr Tyr Val Ala Thr Thr Tyr Phe Pro Leu Leu Pro His Pro
            20                  25                  30

Leu Ser Tyr Phe Ala Trp Pro Leu Tyr Trp Ala Cys Gln Gly Cys Val
        35                  40                  45

Leu Thr Gly Val Trp Val Ile Ala His Glu Cys Gly His His Ala Phe
    50                  55                  60

Ser Asp Tyr Gln Trp Leu Asp Asp Thr Val Gly Leu Ile Phe His Ser
65                  70                  75                  80

Phe Leu Leu Val Pro Tyr Phe Ser Trp Lys Tyr Ser His Arg Arg His
                85                  90                  95

His Ser Asn Thr Gly Ser Leu Glu Arg Asp Glu Val Phe Val Pro Lys
        100                 105                 110
```

```
Lys Lys Ser Asp Ile Lys Trp Tyr Gly Lys Tyr Leu Asn Asn Pro Leu
            115                 120                 125

Gly Arg Thr Val Met Leu Thr Val Gln Phe Thr Leu Gly Trp Pro Leu
130                 135                 140

Tyr Leu Ala Phe Asn Val Ser Gly Arg Pro Tyr Asp Gly Gly Phe Ala
145                 150                 155                 160

Cys His Phe His Pro Asn Ala Pro Ile Tyr Asn Asp Arg Glu Arg Leu
                165                 170                 175

Gln Ile Tyr Ile Ser Asp Ala Gly Ile Leu Ala Val Cys Tyr Gly Leu
            180                 185                 190

Tyr Arg Tyr Ala Ala Val Gln Gly Val Ala Ser Met Val Cys Phe Tyr
        195                 200                 205

Gly Val Pro Leu Leu Ile Val Asn Gly Phe Leu Val Leu Ile Thr Tyr
    210                 215                 220

Leu Gln His Thr His Pro Ser Leu Pro His Tyr Asp Ser Ser Glu Trp
225                 230                 235                 240

Asp Trp Leu Arg Gly Ala Leu Ala Thr Val Asp Arg Asp Tyr Gly Ile
                245                 250                 255

Leu Asn Lys Val Phe His Asn Ile Thr Asp Thr His Val Ala His His
            260                 265                 270

Leu Phe Ser Thr Met Pro His Tyr His Ala Met Glu Ala Thr Lys Ala
        275                 280                 285

Ile Lys Pro Ile Leu Gly Glu Tyr Tyr Gln Phe Asp Gly Thr Pro Val
    290                 295                 300

Val Lys Ala Met Trp Arg Glu Ala Lys Glu Cys Ile Tyr Val Glu Pro
305                 310                 315                 320

Asp Arg Glu Gly Asp Lys Lys
                325

<210> SEQ ID NO 11
<211> LENGTH: 384
<212> TYPE: PRT
<213> ORGANISM: Brassica napus

<400> SEQUENCE: 11

Met Gly Ala Gly Gly Arg Met Gln Val Ser Pro Pro Ser Lys Lys Ser
1               5                   10                  15

Glu Thr Asp Thr Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160
```

```
Lys Lys Ser Asp Ile Lys Trp Tyr Gly Lys Tyr Leu Asn Asn Pro Leu
            165                 170                 175
Gly Arg Thr Val Met Leu Thr Val Gln Phe Thr Leu Gly Trp Pro Leu
        180                 185                 190
Tyr Leu Ala Phe Asn Val Ser Gly Arg Pro Tyr Asp Gly Gly Phe Ala
    195                 200                 205
Cys His Phe His Pro Asn Ala Pro Ile Tyr Asn Asp Arg Glu Arg Leu
210                 215                 220
Gln Ile Tyr Ile Ser Asp Ala Gly Ile Leu Ala Val Cys Tyr Gly Leu
225                 230                 235                 240
Phe Arg Tyr Ala Ala Ala Gln Gly Val Ala Ser Met Val Cys Phe Tyr
                245                 250                 255
Gly Val Pro Leu Leu Ile Val Asn Gly Leu Leu Val Leu Ile Thr Tyr
            260                 265                 270
Leu Gln His Thr His Pro Ser Leu Pro His Tyr Asp Ser Ser Glu Trp
        275                 280                 285
Asp Trp Leu Arg Gly Ala Leu Ala Thr Val Asp Arg Asp Tyr Gly Ile
    290                 295                 300
Leu Asn Lys Val Phe His Asn Ile Thr Asp Thr His Val Ala His His
305                 310                 315                 320
Leu Phe Ser Thr Met Pro His Tyr His Ala Met Glu Ala Thr Lys Ala
                325                 330                 335
Ile Lys Pro Ile Leu Gly Glu Tyr Tyr Gln Phe Asp Gly Thr Pro Val
            340                 345                 350
Val Lys Ala Met Trp Arg Glu Ala Lys Glu Cys Ile Tyr Val Glu Pro
        355                 360                 365
Asp Arg Gln Gly Glu Lys Lys Gly Val Phe Trp Tyr Asn Asn Lys Leu
    370                 375                 380

<210> SEQ ID NO 12
<211> LENGTH: 651
<212> TYPE: DNA
<213> ORGANISM: Brassica napus

<400> SEQUENCE: 12
caagaatttg tcccacagta cacggatgct cagatacact gtccctctcc ccatgctcgc    60
ttaccctctc tatctggtaa atcctaattc ctaattttc ttcctgatta taattacaat   120
tttgaatttt tagatttga gtattaacta aatataaatt aaatttgttt ggggatgact   180
acagtggtac agaagtcctg gtaaagaagg gtcacattat aacccataca gtagtttatt   240
tgccccaagc gagagaaagc ttattgcaac ttcaactact tgctggtcga tcgtgttggc   300
cactcttgtt tatctatcat tcctcgttgg tccagtcaca gttctaaaag tctatggtgt   360
tccttacatt gtaagtttca tatttctt tattatatca ttgctaatat aatttgtttt   420
tgacataaaa gttttggaaa aatttcagat ctttgtaatg tggttggacg ctgtcacgta   480
cttgcatcat catggtcacg atgataagct gccttggtac agaggcaagg taagtagatc   540
aacattattt ataagaagca ataatgatta gtagttgaat aatctgaatt tttgatgttt   600
ttgtacaata ataggaatgg agttatttac gtggaggatt aacaacagtt g            651

<210> SEQ ID NO 13
<211> LENGTH: 651
<212> TYPE: DNA
<213> ORGANISM: Brassica napus

<400> SEQUENCE: 13
```

```
caagaatttg tcccacagta cacggatgct cagatacact gtccctctcc ccatgctcgc    60
ttaccctctc tatctggtaa atcctaattc ctaattttc ttcctgatta taattacaat    120
tttgaatttt tagattttga gtattaacta aatataaatt aaatttgttt ggggatgact   180
acagtggtac agaagtcctg gtaaagaagg gtcacattat aacccataca gtagtttatt   240
tgccccaagc gagagaaagc ttattgcaac ttcaactact tgctggtcga tcgtgttggc   300
cactcttgtt tatctatcat tcctcgttgg tccagtcaca gttctaaaag tctatggtgt   360
tccttacatt gtaagtttca tatatttctt tattatatca ttgctaatat aatttgtttt   420
tgacataaaa gttttggaaa aatttcagat ctttgtaatg tggttggacg ctgtcacgta   480
cttgcatcat catggtcacg atgataagct gccttggtac agaggcaaga taagtagatc   540
aacattattt ataagaagca ataatgatta gtagttgaat aatctgaatt tttgatgtttt  600 ttgtacaata ataggaatgg agttatttac gtggaggatt aacaacagtt g            651
```

<210> SEQ ID NO 14
<211> LENGTH: 23
<212> TYPE: DNA
<213> ORGANISM: Brassica napus

<400> SEQUENCE: 14

```
caagaatttg tcccacagta cac                                           23
```

<210> SEQ ID NO 15
<211> LENGTH: 23
<212> TYPE: DNA
<213> ORGANISM: Brassica napus

<400> SEQUENCE: 15

```
ataaataatg ttgatctact tat                                           23
```

<210> SEQ ID NO 16
<211> LENGTH: 23
<212> TYPE: DNA
<213> ORGANISM: Artificial
<220> FEATURE:
<223> OTHER INFORMATION: Forward primer BNFD32-CF

<400> SEQUENCE: 16

```
caagaatttg tcccacagta cac                                           23
```

<210> SEQ ID NO 17
<211> LENGTH: 22
<212> TYPE: DNA
<213> ORGANISM: Artificial
<220> FEATURE:
<223> OTHER INFORMATION: Reverse primer BNFD32-CR

<400> SEQUENCE: 17

```
caactgttgt taatcctcca cg                                            22
```

<210> SEQ ID NO 18
<211> LENGTH: 19
<212> TYPE: DNA
<213> ORGANISM: Artificial
<220> FEATURE:
<223> OTHER INFORMATION: Primer

<400> SEQUENCE: 18

```
tctccgacca aagctgttt                                                19
```

```
<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
aaggagctgg attcacatgg                                              20

<210> SEQ ID NO 20
<211> LENGTH: 46
<212> TYPE: DNA
<213> ORGANISM: Artificial
<220> FEATURE:
<223> OTHER INFORMATION: Primer with M13 universal sequence at 5' end

<400> SEQUENCE: 20
cacgacgttg taaaacgacg gccagtttct ccgaccaaag ctgttt                 46

<210> SEQ ID NO 21
<211> LENGTH: 27
<212> TYPE: DNA
<213> ORGANISM: Artificial
<220> FEATURE:
<223> OTHER INFORMATION: Primer with 7 extra bases at 5' end

<400> SEQUENCE: 21
gtttcttaag gagctggatt cacatgg                                      27

<210> SEQ ID NO 22
<211> LENGTH: 18
<212> TYPE: DNA
<213> ORGANISM: Artificial
<220> FEATURE:
<223> OTHER INFORMATION: M13 universal primer sequence

<400> SEQUENCE: 22
cacgacgttg taaaacga                                                18
```